(12) United States Patent
Wu et al.

(10) Patent No.: US 10,188,656 B2
(45) Date of Patent: Jan. 29, 2019

(54) METHODS OF TREATMENT OF MALIGNANCIES

(71) Applicant: Agios Pharmaceuticals, Inc., Cambridge, MA (US)

(72) Inventors: Bin Wu, Belmont, MA (US); Sung Eun Choe, Lexington, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/368,439

(22) Filed: Dec. 2, 2016

(65) Prior Publication Data

US 2017/0157132 A1 Jun. 8, 2017

Related U.S. Application Data

(60) Provisional application No. 62/300,721, filed on Feb. 26, 2016, provisional application No. 62/263,580, filed on Dec. 4, 2015.

(51) Int. Cl.
| | | |
|---|---|---|
| *C07D 251/18* | (2006.01) | |
| *C07D 401/14* | (2006.01) | |
| *A61K 31/53* | (2006.01) | |
| *C07D 251/52* | (2006.01) | |
| *A61K 45/06* | (2006.01) | |
| *C12Q 1/6886* | (2018.01) | |

(52) U.S. Cl.
CPC .............. *A61K 31/53* (2013.01); *A61K 45/06* (2013.01); *C07D 251/18* (2013.01); *C07D 251/52* (2013.01); *C07D 401/14* (2013.01); *C12Q 1/6886* (2013.01); *C12Q 2600/106* (2013.01); *C12Q 2600/156* (2013.01)

(58) Field of Classification Search
CPC .. C07D 251/52; C07D 401/14; C07D 403/14; A61K 31/53
USPC .......................................... 544/209; 514/245
See application file for complete search history.

(56) References Cited

U.S. PATENT DOCUMENTS

| | | |
|---|---|---|
| 9,512,107 B2 | 12/2016 | Cianchetta et al. |
| 2002/0051820 A1 | 5/2002 | Shell et al. |
| 2003/0039688 A1 | 2/2003 | Shell et al. |
| 2003/0104053 A1 | 6/2003 | Gusler et al. |
| 2003/0104062 A1 | 6/2003 | Berner et al. |
| 2012/0121515 A1 | 5/2012 | Dang et al. |
| 2013/0190287 A1 | 7/2013 | Cianchetta et al. |
| 2016/0089374 A1 | 3/2016 | Agresta |
| 2016/0158241 A1 | 6/2016 | Travins et al. |
| 2016/0194305 A1 | 7/2016 | Agresta et al. |
| 2017/0037031 A1 | 2/2017 | Zhang |
| 2017/0044139 A1 | 2/2017 | Cianchetta et al. |

FOREIGN PATENT DOCUMENTS

| | | |
|---|---|---|
| CA | 2842635 A1 | 7/2015 |
| WO | WO 2011/050210 A1 | 4/2011 |
| WO | WO 2013/102431 A1 | 7/2013 |
| WO | WO 2013/138237 A1 | 9/2013 |
| WO | WO 2015/006592 A1 | 1/2015 |
| WO | WO 2015/017821 A2 | 2/2015 |
| WO | WO 2016/126798 A1 | 8/2016 |

OTHER PUBLICATIONS

Stein E.Y., Best Practice & Research Clinical Haematology 28 (2015) 112-115.*
Cairns et al., Cancer Discov; 3(7); 730-41, 2013.*
Krell et al., Future Oncol. (2013) 9(12), 1923-1935.*
Reitman et al., J Natl Cancer Inst 2010; 102: 932-941.*
Pimlott SL., Nucl. Med. Commun. 26(3): 183-188, 2005 ,PubMed Abstract provided.*
Cecil Textbook of Medicine, edited by Bennet, J.C., and Plum F., 20th edition, vol. 1, 1004-1010, 1996.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Vippagunta et al., Advanced Drug Delivery Reviews 48: 3-26, 2001.*
Chawla et. al.; CRIPS vol. 5, No. 1, p. 9-12.*
Ulrich, Crystallization, Kirk-Othmer Encyclopedia of Chemical Technology, pp. 1-7, 2002.*
Johnson et al. Clin Cancer Res. Aug. 15, 2014; 20(16): 4186-4192.*
Ohashi et al. Clin Cancer Res. May 1, 2013; 19(9): 2584-2591.*
Aghili et al., "Hydroxyglutaric aciduria and malignant brain tumor: a case report and literature review," *J. Neurooncol.*, 91:233-236 (2009).
Berge et al., "Pharmaceutical salts," J. Pharm. Sci., 66(1):1-19 (1977).
Caunt et al., "MEK1 and MEK2 inhibitors and cancer therapy: the long and winding road," *Nature Rev. Cancer*, 15(10):577-592 (2015).
Chen et al., "Cancer-associated IDH2 mutants drive an acute myeloid leukemia that is susceptible to Brd4 inhibition," *Genes Dev.*, 27(18):1974-1985 (2013).
Dang et al., "Cancer-associated IDH1 mutations produce 2-hydroxyglutarate," *Nature*, 462(7274):739-744 (2009).
Foundation One Heme Panel, Technical information and test overview, Retrieved on Mar. 9, 2017. Retrieved from the internet: URL: http://foundationone.com/learn.php.
Geisbrecht et al., "The human PICD gene encodes a cytoplasmic and peroxisomal NADP(+)-dependent isocitrate dehydrogenase," *J. Biol. Chem.*, 274(43):30527-30533 (1999).
Genbank Accession No. NM_002168.2 (Feb. 22, 2014).
Genbank Accession No. NM_005896.2 (Sep. 2, 2013).
Genbank Accession No. NP_002159.2 (Apr. 30, 2016).
Genbank Accession No. NP_005887.2 (Jan. 4, 2017).
Gerhard et al., "The status, quality, and expansion of the NIH full-length cDNA project: the Mammalian Gene Collection (MGC)," *Genome Res.*, 14(10B):2121-2127 (2004).
Greenberg et al., "Revised international prognostic scoring system for myelodysplastic syndromes,"*Blood*, 120(12):2454-2465 (2012).
Kölker et al., "NMDA receptor activation and respiratory chain complex V inhibition contribute to neurodegeneration in d-2-hydroxyglutaric aciduria," *Eur. J. Neurosci.*, 16(1):21-28 (2002).

(Continued)

*Primary Examiner* — Venkataraman Balasubramanian

(74) *Attorney, Agent, or Firm* — Jones Day

(57) ABSTRACT

Provided are methods and compositions for treating cancers in patients carrying an IDH1 mutation or IDH2 mutation.

8 Claims, 11 Drawing Sheets

(56) References Cited

OTHER PUBLICATIONS

Kölker et al., "White matter disease in cerebral organic acid disorders: clinical implications and suggested pathomechanisms," *Neuropediatrics*, 33(5):225-231 (2002).
Komanduri et al., "Diagnosis and therapy of acute myeloid leukemia in the era of molecular risk stratification," *Ann. Rev. Med., Selected Topics in the Clinicalsciences*, 67(1):59-72 (2016).
Latini et al., "D-2-hydroxyglutaric acid induces oxidative stress in cerebral cortex of young rats," *Eur. J. Neurosci.*, 17(10):2017-2022 (2003).
Luo et al., "Simultaneous determination of multiple intracellular metabolites in glycolysis, pentose phosphate pathway and tricarboxylic acid cycle by liquid chromatography-mass spectrometry," *J. Chromatogr.*, 1147(2):153-164 (2007).
Munger et al., "Systems-level metabolic flux profiling identifies fatty acid synthesis as a target for antiviral therapy," *Nat. Biotechnol.*, 26(10):1179-1186 (2008).
Nekrutenko et al., "Cytosolic isocitrate dehydrogenase in humans, mice, and voles and phylogenetic analysis of the enzyme family," *Mol. Biol. Evol.*, 15(12):1674-1684 (1998).
Papaemmanuil et al., "Genomic Classification in Acute Myeloid Leukemia,"*N. Engl. J. Med.*, 375(9):900-901 (2016).
Prior et al., "A comprehensive survey of Ras mutations in cancer," *Cancer Res.*, 72(10):2457-2467 (2012).
Sjöblom et al., "The consensus coding sequences of human breast and colorectal cancers," *Science*, 314(5797):268-274 (2006).
Struys et al., "Mutations in the D-2-hydroxyglutarate dehydrogenase gene cause D-2-hydroxyglutaric aciduria," *Am. J. Hum. Genet.*, 76:358-360 (2005).
Takashima et al., "Targeting the RAS oncogene," *Expert Opin. Ther. Targets*, 17(5):507-531 (2013).
Wajner et al., "The role of oxidative damage in the neuropathology of organic acidurias: insights from animal studies," *J. Inherit. Metab. Dis.*, 27(4):427-448 (2004).
Wiemann et al., "Toward a catalog of human genes and proteins: sequencing and analysis of 500 novel complete protein coding human cDNAs," *Genome Res.*, 11(3):422-435 (2001).

* cited by examiner n = 14

METHODS OF TREATMENT OF MALIGNANCIES

CROSS REFERENCE TO RELATED APPLICATIONS

This application claims the benefit of the priority of U.S. Provisional Application Nos. 62/300,721, filed Feb. 26, 2016, and 62/263,580, filed Dec. 4, 2015, the disclosure of each of which is incorporated herein by reference in its entirety.

FIELD

In certain aspects, provided herein are methods of treating malignancies including hematological malignancies and solid tumors characterized by the presence of a mutant allele of IDH1 or IDH2, and the absence of a mutant allele of NRAS. In one embodiment, the methods for treating a malignancy comprise administering an IDH1 inhibitor or an IDH2 inhibitor in combination with one or more compounds that target RAS pathways wherein the malignancy is characterized by the presence of a mutant allele of IDH1 or IDH2 respectively, and a mutant allele of NRAS. In one aspect, provided herein is an IDH2 inhibitor for use in methods of treating malignancies including hematological malignancies and solid tumors characterized by the presence of a mutant allele of IDH2, and the absence of a mutant allele of NRAS. In one embodiment, an IDH2 inhibitor can be provided in combination with one or more compounds that target RAS pathways for use in methods for treating a malignancy, wherein the malignancy is characterized by the presence of a mutant allele of IDH2, and a mutant allele of NRAS.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December 2008) to UniProtKB; Kullmann et al., Submitted (June 1996) to the EMBL/GenBank/DDBJ databases; and Sjoeblom et al., Science 314:268-274(2006).

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November 1992) to the EMBL/GenBank/DDBJ databases; and The MGC Project Team, Genome Res. 14:2121-2127 (2004).

Non-mutant, e.g., wild type, IDH1 and IDH2 catalyze the oxidative decarboxylation of isocitrate to α-ketoglutarate (α-KG) thereby reducing NAD$^+$(NADP$^+$) to NADH (NADPH), e.g., in the forward reaction:

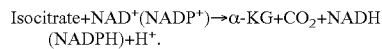

It has been discovered that mutations of IDH2 present in certain cancer cells result in a new ability of the enzyme to catalyze the NADPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

The development of selective inhibitors of IDH1 or IDH2 mutant enzymes has provided the possibility of therapeutic benefit to cancer patients carrying the IDH1 or IDH2 mutations. There is a need for improved therapies for treating cancer patients carrying IDH1 or IDH2 mutations.

SUMMARY

In one embodiment, provided herein are methods of treating hematologic malignancies by administering to a subject a therapeutically effective amount of a mutant IDH2 inhibitor, wherein the hematologic malignancy is characterized by the presence of a mutant allele of IDH2 and the absence of a mutant allele of NRAS. In one embodiment, the hematologic malignancy is an advanced hematologic malignancy. Also provided herein is a mutant IDH2 inhibitor for use in the methods of treating hematologic malignancies, wherein the hematologic malignancy is characterized by the presence of a mutant allele of IDH2 and the absence of a mutant allele of NRAS.

In one embodiment, provided herein are methods of treating hematologic malignancies by administering to a subject a therapeutically effective amount of a mutant IDH2 inhibitor in combination with a therapeutically effective amount of one or more compounds that target RAS pathways, wherein the hematologic malignancy is characterized by the presence of a mutant allele of IDH2 and a mutant allele of NRAS. In one embodiment, the hematologic malignancy is an advanced hematologic malignancy. Also provided herein is an IDH2 inhibitor in combination with a therapeutically effective amount of one or more compounds that target RAS pathways for use in the methods of treating hematologic malignancies, wherein the hematologic malignancy is characterized by the presence of a mutant allele of IDH2 and a mutant allele of NRAS.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and the absence of a mutant allele of NRAS, comprising administering to a subject a therapeutically effective amount of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, or a pharmaceutically acceptable salt, solvate, tautomer, stereoisomer, isotopologue, prodrug or a polymorph thereof (COMPOUND 1). In one embodiment, the hematologic malignancy is an advanced hematologic malignancy. In one embodiment, the advanced hematologic malignancy is AML. In one embodiment, the advanced hematologic malignancy is relapsed or refractory AML.

Also provided herein is COMPOUND 1 for use in the method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and the absence of a mutant allele of NRAS. In one embodiment, the advanced hematologic malignancy is AML, characterized by the presence of a mutant allele of IDH2 and the absence of a mutant allele of NRAS. In one embodiment, the advanced hematologic malignancy is relapsed or refractory AML, characterized by the presence of a mutant allele of IDH2 and the absence of a mutant allele of NRAS.

In one aspect, provided is COMPOUND 1 for use in a method of treating acute myelogenous leukemia (AML) characterized by the presence of a mutant allele of IDH2 and the absence of a mutant allele of NRAS. In one aspect, provided is COMPOUND 1 for use in a method of treating relapsed or refractory acute myelogenous leukemia (AML) characterized by the presence of a mutant allele of IDH2 and the absence of a mutant allele of NRAS.

In one embodiment, provided is COMPOUND 1 for use in a method of treating myelodysplastic syndrome (MDS) characterized by the presence of a mutant allele of IDH2 and the absence of a mutant allele of NRAS.

In one embodiment, provided is COMPOUND 1 for use in a method of treating chronic myelomonocytic leukemia (CMML) characterized by the presence of a mutant allele of IDH2 and the absence of a mutant allele of NRAS.

In one embodiment, provided is COMPOUND 1 for use in a method of treating myeloid sarcoma characterized by the presence of a mutant allele of IDH2 and the absence of a mutant allele of NRAS.

In one embodiment, provided is COMPOUND 1 for use in a method of treating multiple myeloma characterized by the presence of a mutant allele of IDH2 and the absence of a mutant allele of NRAS.

In one embodiment, provided is COMPOUND 1 for use in a method of treating lymphoma (e.g., T-cell lymphoma or B-cell lymphoma) characterized by the presence of a mutant allele of IDH2 and the absence of a mutant allele of NRAS.

In one embodiment, provided is COMPOUND 1 for use in a method of treating angioimmunoblastic T-cell lymphoma (AITL) characterized by the presence of a mutant allele of IDH2 and the absence of a mutant allele of NRAS.

In one embodiment, provided is COMPOUND 1 for use in a method of treating blastic plasmacytoid dendritic cell neoplasm characterized by the presence of a mutant allele of IDH2 and the absence of a mutant allele of NRAS.

In one embodiment, provided herein is a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and a mutant allele of NRAS comprising administering to the subject a therapeutically effective amount of COMPOUND 1 in combination with a therapeutically effective amount of one or more compounds that target RAS pathways. In one embodiment, provided herein is COMPOUND 1 in combination with one or more compounds that target RAS pathways for use in a method of treating hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and a mutant allele of NRAS. In one embodiment, provided herein is COMPOUND 1 in combination with one or more compounds that target RAS pathways for use in a method of treating acute myelogenous leukemia (AML) characterized by the presence of a mutant allele of IDH2 and a mutant allele of NRAS. In one embodiment, provided herein is COMPOUND 1 in combination with one or more compounds that target RAS pathways for use in a method of treating myelodysplastic syndrome (MDS) characterized by the presence of a mutant allele of IDH2 and a mutant allele of NRAS. In one embodiment, provided herein is a COMPOUND 1 in combination with one or more compounds that target RAS pathways for use in the method of treating chronic myelomonocytic leukemia (CMML) characterized by the presence of a mutant allele of IDH2 and a mutant allele of NRAS. In certain embodiments, provided herein is COMPOUND 1 in combination with one or more compounds that target RAS pathways for use in a method of treating myeloid sarcoma characterized by the presence of a mutant allele of IDH2 and a mutant allele of NRAS. In one embodiment, provided herein is COMPOUND 1 in combination with one or more compounds that target RAS pathways for use in a method of treating multiple myeloma characterized by the presence of a mutant allele of IDH2 and a mutant allele of NRAS. In one embodiment, provided herein is COMPOUND 1 in combination with one or more compounds that target RAS pathways for use in a method of treating lymphoma (e.g., T-cell lymphoma or B-cell lymphoma) characterized by the presence of a mutant allele of IDH2 and a mutant allele of NRAS. In one embodiment, provided herein is COMPOUND 1 in combination with one or more compounds that target RAS pathways for use in a method of treating angioimmunoblastic T-cell lymphoma (AITL) characterized by the presence of a mutant allele of IDH2 and a mutant allele of NRAS. In one embodiment, provided herein is COMPOUND 1 in combination with one or more compounds that target RAS pathways for use in a method of treating blastic plasmacytoid dendritic cell neoplasm characterized by the presence of a mutant allele of IDH2 and a mutant allele of NRAS.

In one embodiment, COMPOUND 1 is administered to the subject in combination with a therapeutically effective amount of a MEK kinase inhibitor selected from trametinib, selumetinib, binimetinib, PD-325901, cobimetinib, CI-1040 and PD035901. In one embodiment, the hematologic malignancy is an advanced hematologic malignancy. In one embodiment, the advanced hematologic malignancy is AML, characterized by the presence of a mutant allele of IDH2 and the absence of a mutant allele of NRAS. In one embodiment, the advanced hematologic malignancy is relapsed or refractory AML, characterized by the presence of a mutant allele of IDH2 and the absence of a mutant allele of NRAS.

In one embodiment, COMPOUND 1 is administered to the subject in combination with trametinib. In one embodiment, COMPOUND 1 is administered to the subject in combination with selumetinib. In one embodiment, COMPOUND 1 is administered to the subject in combination with binimetinib. In one embodiment, COMPOUND 1 is administered to the subject in combination with PD-325901. In one embodiment, COMPOUND 1 is administered to the subject in combination with cobimetinib. In one embodiment, COMPOUND 1 is administered to the subject in combination with CI-1040. In one embodiment, COMPOUND 1 is administered to the subject in combination with PD035901.

In one embodiment, provided herein are methods of treating solid tumors by administering to a subject a therapeutically effective amount of a mutant IDH2 inhibitor, wherein the solid tumor is characterized by the presence of a mutant allele of IDH2 and the absence of a mutant allele of NRAS. In one embodiment, the solid tumor is an advanced solid tumor.

In one embodiment, provided herein is a mutant IDH2 inhibitor for use in a method of treating solid tumors, wherein the solid tumor is characterized by the presence of a mutant allele of IDH2 and the absence of a mutant allele of NRAS.

In one embodiment, provided herein are methods of treating solid tumors by administering to a subject a therapeutically effective amount of a mutant IDH2 inhibitor in combination with a therapeutically effective amount of one or more compounds that target RAS pathways, wherein the solid tumor is characterized by the presence of a mutant allele of IDH2 and a mutant allele of NRAS. In one aspect, provided herein is a mutant IDH2 inhibitor in combination with one or more compounds that target RAS pathways for use in the methods of treating solid tumors, wherein the solid tumor is characterized by the presence of a mutant allele of IDH2 and a mutant allele of NRAS. In one embodiment, the solid tumor is an advanced solid tumor.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and the absence of a mutant allele of NRAS, comprising administering to a subject a therapeutically effective amount of COMPOUND 1.

In one embodiment, provided herein is a method of treating solid tumors, such as glioma, melanoma, chondrosarcoma, or cholangiocarcinoma (e.g., glioma), or treating angioimmunoblastic T-cell lymphoma (AITL), each characterized by the presence of a mutant allele of IDH2 and a mutant allele of NRAS, in a subject comprising administering to a subject a therapeutically effective amount of COMPOUND 1 in combination with a therapeutically effective amount of one or more compounds that target RAS pathways. In one embodiment, COMPOUND 1 is administered to the subject in combination with a therapeutically effective amount of a MEK kinase inhibitor selected from trametinib, selumetinib, binimetinib, PD-325901, cobimetinib, CI-1040 and PD035901.

In one embodiment, COMPOUND 1 is administered to the subject in combination with trametinib. In one embodiment, COMPOUND 1 is administered to the subject in combination with selumetinib. In one embodiment, COMPOUND 1 is administered to the subject in combination with binimetinib. In one embodiment, COMPOUND 1 is administered to the subject in combination with PD-325901. In one embodiment, COMPOUND 1 is administered to the subject in combination with cobimetinib. In one embodiment, COMPOUND 1 is administered to the subject in combination with CI-1040. In one embodiment, COMPOUND 1 is administered to the subject in combination with PD035901.

BRIEF DESCRIPTION OF THE DRAWINGS

FIG. 9B illustrates variant allele frequency of NRAS mutation in patients by response.

FIGS. 10 A-C provide analysis of mutational burden and response to COMPOUND 2.

DETAILED DESCRIPTION

Figure 1:
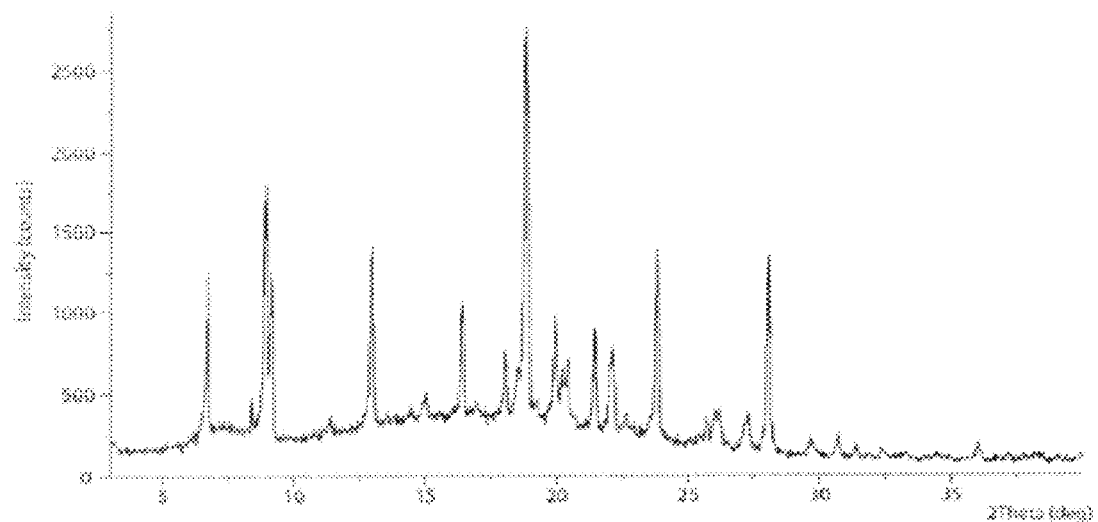
FIG. 1 is an X-ray powder diffractogram (XPRD) of COMPOUND 1 form 1.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term a "mutant IDH2 inhibitor" or "inhibitor of IDH2 mutant(s)" means a molecule e.g., a polypeptide, peptide, or small molecule (e.g., a molecule of less than 1,000 daltons), or aptomer, that binds to an IDH2 mutant subunit and inhibits neoactivity, e.g., by inhibiting formation of a dimer, e.g., a homodimer of mutant IDH2 subunits or a heterodimer of a mutant and a wildype subunit. In some embodiments, the neoactivity inhibition is at least about 60%, 70%, 80%, 90%, 95% or 99% as compared to the activity in the absence of the mutant IDH2 inhibitor. In one embodiment, the mutant IDH2 inhibitor is COMPOUND 1 (2-methyl-1-[(4-[6-(trifluoromethyl)pyridin-2-yl]-6-[2-(trifluoromethyl)pyridin-4-yl]amino-1,3,5-triazin-2-yl)amino]propan-2-ol, or a pharmaceutically acceptable salt, solvate, tautomer, stereoisomer, isotopologue, prodrug, metabolite, or a polymorph thereof).

The term a "mutant IDH1 inhibitor" or "inhibitor of IDH1 mutant(s)" means a molecule e.g., a polypeptide, peptide, or small molecule (e.g., a molecule of less than 1,000 daltons), or aptomer, that binds to an IDH1 mutant subunit and inhibits neoactivity, e.g., by inhibiting formation of a dimer, e.g., a homodimer of mutant IDH1 subunits or a heterodimer of a mutant and a wildype subunit. In some embodiments, the neoactivity inhibition is at least about 60%, 70%, 80%, 90%, 95% or 99% as compared to the activity in the absence of the mutant IDH1 inhibitor. In one embodiment, the mutant IDH1 inhibitor is COMPOUND 2 ((S)—N—((S)-1-(2-chlorophenyl)-2-((3,3-difluorocyclobutyl)amino)-2-oxoethyl)-1-(4-cyanopyridin-2-yl)-N-(5-fluoropyridin-3-yl)-5-oxopyrrolidine-2-carboxamide, a pharmaceutically acceptable salt, solvate, tautomer, stereoisomer, isotopologue, prodrug, or a polymorph thereof).

As used herein, the term "wild type" refers to the typical or most common form of a characteristic (for example, gene sequence or presence, or protein sequence, presence, level or activity), as it occurs in nature, and the reference against which all others are compared. As will be understood by one skilled in the art, when used herein, wild type refers to the typical gene sequence(s) or gene expression levels as they most commonly occur in nature.

As used herein, "co-occurring mutation" refers to one or more gene mutations that are present in a cancer subject herein in addition to an IDH1 or an IDH2 mutation.

The term "RAS pathway inhibitor" or "RAS targeting compound" refers to a compound that inhibits RAS proteins association with the plasma membrane as well as compounds that target the signalling cascade downstream of RAS, including the RAF-MEK-ERK signalling cascade. Exemplary RAS pathway inhibitors for use herein include, but are not limited to trametinib (GSK1120212), selumetinib, binimetinib (MEK162), PD-325901, cobimetinib (XL518), CI-1040 and PD035901.

The term "elevated levels of 2HG" means 10%, 20% 30%, 50%, 75%, 100%, 200%, 500% or more 2HG is present in a subject that carries a mutant IDH1 allele than is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

The terms "inhibit" or "prevent" include both complete and partial inhibition and prevention. An inhibitor may completely or partially inhibit the intended target.

The term "subject" is intended to include human and non-human animals. Exemplary human subjects include a human patient (referred to as a patient) having a disorder, e.g., a disorder described herein or a normal subject. The term "non-human animals" of one aspect of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

The term "treat" means decrease, suppress, attenuate, diminish, arrest, or stabilize the development or progression of a disease/disorder (e.g., an hematologic malignancy, including an advanced hematologic malignancy, such as acute myelogenous leukemia (AML), myelodysplastic syndrome (MDS), myeloproliferative neoplasms (MPN), chronic myelomonocytic leukemia (CMML), B-acute lymphoblastic leukemias (B-ALL), or lymphoma (e.g., T-cell lymphoma), or a solid tumor, including glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1; or acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, or solid tumors, such as glioma, melanoma, chondrosarcoma, or cholangiocarcinoma (e.g., glioma), or angioimmunoblastic T-cell lymphoma (AITL), each characterized by the presence of a mutant allele of IDH2), lessen the severity of the disease/disorder or improve the symptoms associated with the disease/disorder. In one embodiment, the advanced hematologic malignancy is relapsed or refractory. In one embodiment, the solid tumor is relapsed or refractory.

An amount of a compound, including a pharmaceutically acceptable salt, solvate, tautomer, stereoisomer, isotopologue, prodrug or a polymorph thereof, effective to treat a disorder, or a "therapeutically effective amount" or "therapeutically effective dose" refers to an amount of the compound, including a pharmaceutically acceptable salt, solvate, tautomer, stereoisomer, isotopologue, prodrug, or a polymorph thereof, which is effective, upon single or multiple dose administration to a subject, in treating a cell, or in curing, alleviating, relieving or improving a subject with a disorder beyond that expected in the absence of such treatment.

The term "co-administering" as used herein with respect to additional cancer therapeutic agents means that the additional cancer therapeutic agent may be administered together with a compound provided herein as part of a single dosage form (such as a composition comprising a compound and a second therapeutic agent as described above) or as separate, multiple dosage forms. Alternatively, the additional cancer therapeutic agent may be administered prior to, consecutively with, or following the administration of a compound provided herein. In such combination therapy treatment, both the compounds provided herein and the second therapeutic agent(s) are administered by conventional methods. The administration of a composition comprising both a compound provided herein and a second therapeutic agent, to a subject does not preclude the separate administration of that same therapeutic agent, any other second therapeutic agent or any compound provided herein to said subject at another time during a course of treatment. The term "co-administering" as used herein with respect to an additional cancer treatment means that the additional cancer treatment may occur prior to, consecutively with, concurrently with or following the administration of a compound provided herein.

The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%.

The term "enriched" means that at least the designated percentage of a preparation is the compound having a selected stereochemistry at one or more selected stereocenters.

The term "crystalline" refers to a solid having a highly regular chemical structure. In particular, a crystalline COMPOUND 1 may be produced as one or more single crystalline forms of COMPOUND 1 and a crystalline COMPOUND 2 may be produced as one or more single crystalline forms of COMPOUND 2. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of COMPOUND 1 is considered to be a distinct single crystalline form herein, and each distinct polymorph and pseudopolymorph of COMPOUND 2 is considered to be a distinct single crystalline form herein.

The term "substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%.

In some embodiments, substantially crystalline COMPOUND 1 refers to a COMPOUND 1 that is at least 70% crystalline. In other embodiments, substantially crystalline COMPOUND 1 refers to a COMPOUND 1 that is at least 90% crystalline. In some embodiments, substantially crystalline COMPOUND 2 refers to a COMPOUND 2 that is at least 70% crystalline. In other embodiments, substantially crystalline COMPOUND 2 refers to a COMPOUND 2 that is at least 90% crystalline.

The term "isolated" refers to forms that may be at least a particular weight percent of a particular crystalline form of compound. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is $H_2O$ that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

The term "pharmaceutically acceptable carrier or adjuvant" refers to a carrier or adjuvant that may be administered to a subject, together with a compound of one aspect of this invention, and which does not destroy the pharmacological activity thereof and is nontoxic when administered in doses sufficient to deliver a therapeutic amount of the compound.

The term "a pharmaceutically-acceptable salt" as used herein refers to non-toxic acid or base addition salts of the compound to which the term refers. Examples of pharmaceutically acceptable salts are discussed in Berge et al., 1977, "Pharmaceutically Acceptable Salts." *J. Pharm. Sci.* Vol. 66, pp. 1-19.

The term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Compounds

A. Compound 1

In one embodiment, COMPOUND 1 is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, or a pharmaceutically acceptable salt, solvate, tautomer, stereoisomer, isotopologue, prodrug, metabolite, or a polymorph thereof, having the following formula:

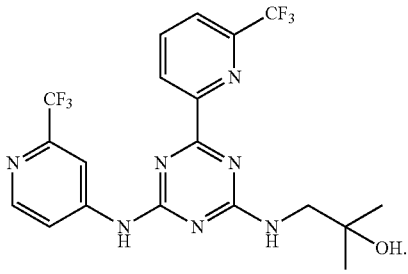 [SMILES: CC(C)(O)CNc1nc(Nc2ccnc(C(F)(F)F)c2)nc(-c2cccc(C(F)(F)F)n2)n1]

COMPOUND 1 may also comprise one or more isotopic substitutions ("Isotopologues"). For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. For example, COMPOUND 1 is enriched in a specific isotopic form of H, C and/or O by at least about 60%, 65%, 70%, 75%, 80%, 85%, 90%, 95%, 96%, 97%, 98%, or 99%.

COMPOUND 1 in certain embodiments may also be represented in multiple tautomeric forms, in such instances, one aspect of the invention expressly includes all tautomeric forms of COMPOUND 1 described herein, even though only a single tautomeric form may be represented (e.g., keto-enol tautomers). All such isomeric forms of COMPOUND 1 are expressly included herein. Synthesis of COMPOUND 1 is described in US published application US-2013-0190287-A1 published Jul. 25, 2013, which is incorporated by reference in its entirety.

It may be convenient or desirable to prepare, purify, and/or handle a corresponding salt of COMPOUND 1, for example, a pharmaceutically-acceptable salt. Examples of pharmaceutically acceptable salts are discussed in Berge et al., 1977, "Pharmaceutically Acceptable Salts." *J. Pharm. Sci. Vol.* 66, pp. 1-19.

For example, if COMPOUND 1 is anionic, or has a functional group which may be anionic (e.g., —NH— may be —N—$^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If COMPOUND 1 is cationic, or has a functional group that may be cationic (e.g., —NHR may be —$NH_2R^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. In one embodiment, COMPOUND 1 comprises the mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol. Examples of suitable polymeric organic anions include, but are not limited to, those derived from the following polymeric acids: tannic acid, carboxymethyl cellulose.

COMPOUND 1 for use in the methods and pharmaceutical compositions provided herein therefore includes the COMPOUND 1 itself, as well as its pharmaceutically acceptable salts, solvates, tautomers, stereoisomers, isotopologues, prodrugs, metabolites, or polymorphs. Metabolites of COMPOUND 1 are disclosed in patent application publication WO2015/006592, which is incorporated herein by reference in its entirety. COMPOUND 1 provided herein may be modified and converted to a prodrug by appending appropriate functionalities to enhance selected biological properties, e.g., targeting to a particular tissue. Such modifications (i.e., prodrugs) are known in the art and include those which increase biological penetration into a given biological compartment (e.g., blood, lymphatic system, central nervous system), increase oral availability, increase solubility to allow administration by injection, alter metabolism and alter rate of excretion. Examples of prodrugs include esters (e.g., phosphates, amino acid (e.g., valine) esters), carbamates and other pharmaceutically acceptable derivatives, which, upon administration to a subject, are capable of providing active compounds.

It has been found that COMPOUND 1 can exist in a variety of solid forms. In one embodiment, provided herein are solid forms that include neat crystal forms. In another embodiment, provided herein are solid forms that include solvated forms and amorphous forms. The present disclosure provides certain solid forms of COMPOUND 1. In certain embodiments, the present disclosure provides compositions comprising COMPOUND 1 in a form described herein. In some embodiments of provided compositions, COMPOUND 1 is present as a mixture of one or more solid forms; in some embodiments of provided compositions, COMPOUND 1 is present in a single form.

In one embodiment, COMPOUND 1 is a single crystalline form, or any one of the single crystalline forms described herein. Synthesis of crystalline forms of COMPOUND 1 is described in the international application publication WO 2015/017821 published Feb. 5, 2015 and the U.S. provisional application Ser. No. 61/112,127, filed Feb. 4, 2015, both incorporated by reference herein in their entireties. Also provided are pharmaceutical compositions comprising at least one pharmaceutically acceptable carrier or diluent; and COMPOUND 1, wherein COMPOUND 1 is a single crystalline form, or any one of the crystalline forms being described herein. Also provided are uses of COMPOUND 1, wherein COMPOUND 1 is a single crystalline form, or any one of the single crystalline forms described herein, to prepare a pharmaceutical composition.

Provided herein is an assortment of characterizing information to describe the crystalline forms of COMPOUND 1. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

In one embodiment, at least a particular percentage by weight of COMPOUND 1 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of COMPOUND 1 is crystalline, the remainder of COMPOUND 1 is the amorphous form of COMPOUND 1. Non-limiting examples of crystalline COMPOUND 1 include a single crystalline form of COMPOUND 1 or a mixture of different single crystalline forms. In some embodiments, COMPOUND 1 is at least 90% by weight crystalline. In some other embodiments, COMPOUND 1 is at least 95% by weight crystalline.

In another embodiment, a particular percentage by weight of the crystalline COMPOUND 1 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, COMPOUND 1 is at least 90% by weight of a single crystalline form. In another embodiment, COMPOUND 1 is at least 95% by weight of a single crystalline form.

In the following description of COMPOUND 1, embodiments of the invention may be described with reference to a particular crystalline form of COMPOUND 1, as characterized by one or more properties as discussed herein. The descriptions characterizing the crystalline forms may also be used to describe the mixture of different crystalline forms that may be present in a crystalline COMPOUND 1. However, the particular crystalline forms of COMPOUND 1 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1 to 6 may vary by ±0.2° depending upon the instrument used to obtain the data. The intensity of the XRPD peaks described in Tables 1 to 6 may vary by 10%.

Form 1

In one embodiment, a single crystalline form, Form 1, of COMPOUND 1 is characterized by the X-ray powder diffraction (XRPD) pattern shown in FIG. 1, and data shown in Table 1 obtained using CuKα radiation. In a particular embodiment, the polymorph can be characterized by one or more of the peaks taken from FIG. 1, as shown in Table 1. For example, the polymorph can be characterized by one or two or three or four or five or six or seven or eight or nine of the peaks shown in Table 1.

TABLE 1

| Angle 2-θ | Intensity % |
| --- | --- |
| 6.7 | 42.2 |
| 8.9 | 61.8 |
| 9.1 | 41.9 |
| 13.0 | 46.7 |
| 16.4 | 33.2 |
| 18.9 | 100.0 |
| 21.4 | 27.3 |
| 23.8 | 49.2 |
| 28.1 | 47.5 |

In another embodiment, Form 1 can be characterized by the peaks identified at 2θ angles of 8.9, 13.0, 18.9, 23.8, and 28.1°. In another embodiment, Form 1 can be characterized by the peaks identified at 2θ angles of 8.9, 18.9, and 23.8°.

Form 2

Figure 2:
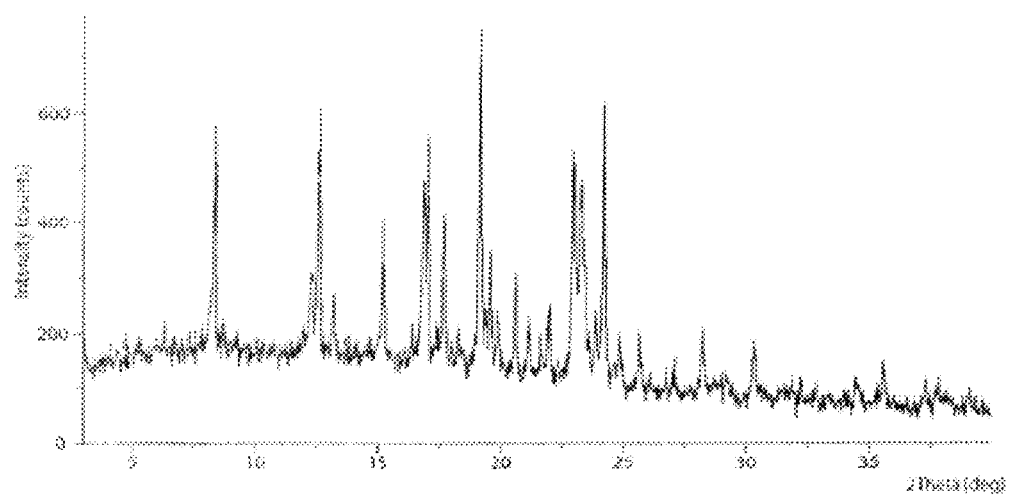
FIG. 2 is an X-ray powder diffractogram (XPRD) of COMPOUND 1 form 2.

In one embodiment, a single crystalline form, Form 2, of COMPOUND 1 is characterized by the X-ray powder diffraction (XRPD) pattern shown in FIG. 2, and data shown in Table 2, obtained using CuKα radiation. In a particular embodiment, the polymorph can be characterized by one or more of the peaks taken from FIG. 2, as shown in Table 2. For example, the polymorph can be characterized by one or two or three or four or five or six or seven or eight or nine of the peaks shown in Table 2.

TABLE 2

| Angle 2-θ | Intensity % |
| --- | --- |
| 8.4 | 65.2 |
| 12.7 | 75.5 |
| 16.9 | 57.9 |
| 17.1 | 69.4 |
| 17.7 | 48.6 |
| 19.2 | 100.0 |
| 23.0 | 69.7 |
| 23.3 | 61.1 |
| 24.2 | 87.3 |

In another embodiment, Form 2 can be characterized by the peaks identified at 2θ angles of 12.7, 17.1, 19.2, 23.0, and 24.2°. In another embodiment, Form 2 can be characterized by the peaks identified at 2θ angles of 12.7, 19.2, and 24.2°.

Form 3

Figure 3:
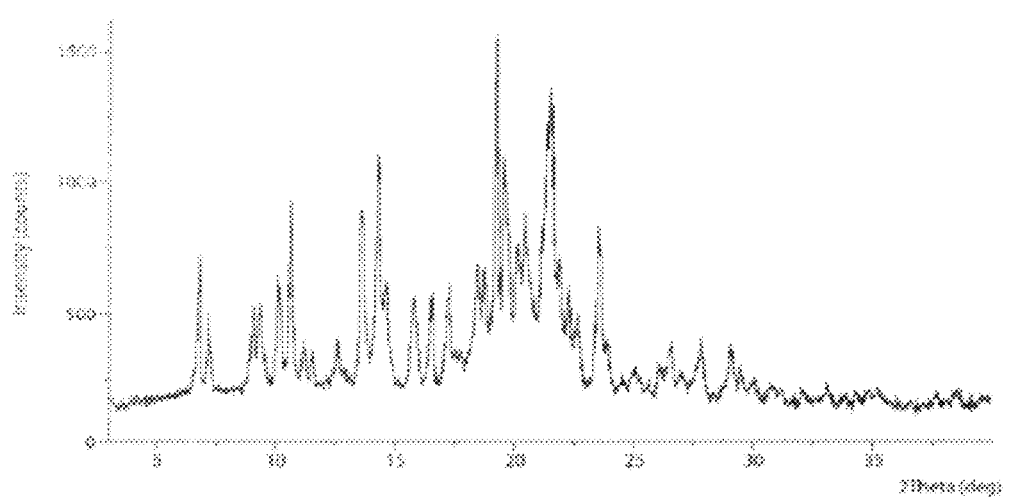
FIG. 3 is an X-ray powder diffractogram (XPRD) of COMPOUND 1 form 3.

In one embodiment, a single crystalline form, Form 3, of COMPOUND 1 is characterized by the X-ray powder diffraction (XRPD) pattern shown in FIG. 3, and data shown in Table 3, obtained using CuKα radiation. In a particular embodiment, the polymorph can be characterized by one or more of the peaks taken from FIG. 3, as shown in Table 3. For example, the polymorph can be characterized by one or two or three or four or five or six or seven or eight or nine of the peaks shown in Table 3.

TABLE 3

| Angle 2-θ | Intensity % |
| --- | --- |
| 6.8 | 35.5 |
| 10.1 | 30.7 |
| 10.6 | 53.1 |
| 13.6 | 46.0 |
| 14.2 | 63.8 |
| 17.2 | 26.4 |
| 18.4 | 34.0 |
| 19.2 | 100.0 |
| 23.5 | 3.8 |

In another embodiment, Form 3 can be characterized by the peaks identified at 2θ angles of 6.8, 10.6, 13.6, 14.2, and 19.2°. In another embodiment, Form 3 can be characterized by the peaks identified at 2θ angles of 10.6, 14.2, and 19.2°.

Form 4

Figure 4:
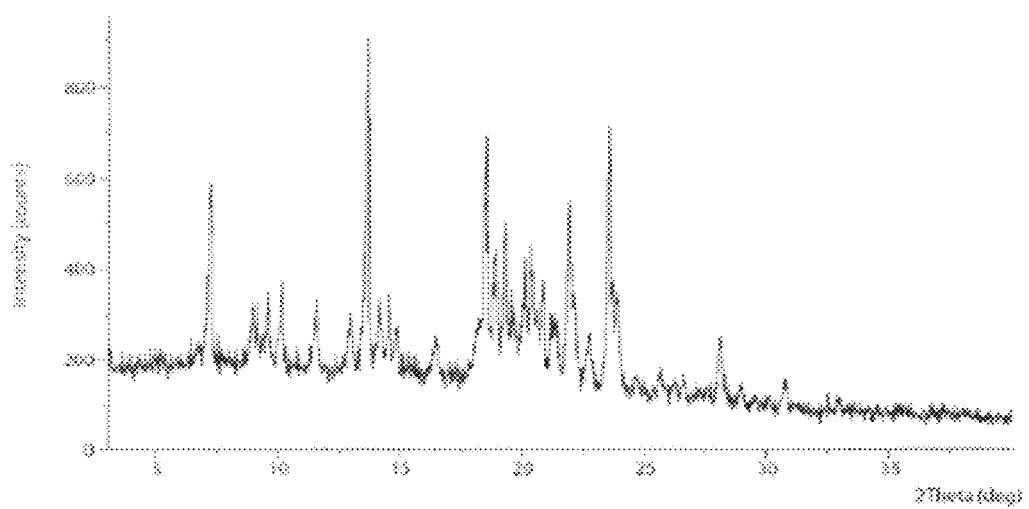
FIG. 4 is an X-ray powder diffractogram (XPRD) of COMPOUND 1 form 4.

In one embodiment, a single crystalline form, Form 4, of COMPOUND 1 is characterized by the X-ray powder diffraction (XRPD) pattern shown in FIG. 4, and data shown in Table 4, obtained using CuKα radiation. In a particular embodiment, the polymorph can be characterized by one or more of the peaks taken from FIG. 4, as shown in Table 4. For example, the polymorph can be characterized by one or two or three or four or five or six or seven or eight or nine of the peaks shown in Table 4.

TABLE 4

| Angle 2-θ | Intensity % |
| --- | --- |
| 7.2 | 53.3 |
| 10.1 | 26.7 |
| 11.5 | 20.5 |
| 13.6 | 100.0 |
| 18.5 | 72.0 |
| 19.3 | 46.9 |
| 20.3 | 39.4 |
| 21.9 | 55.4 |
| 23.5 | 77.5 |

In another embodiment, Form 4 can be characterized by the peaks identified at 2θ angles of 7.2, 13.6, 18.5, 19.3, 21.9, and 23.5°. In another embodiment, Form 4 can be characterized by the peaks identified at 2θ angles of 13.6, 18.5, and 23.5°.

Form 5

Figure 5:
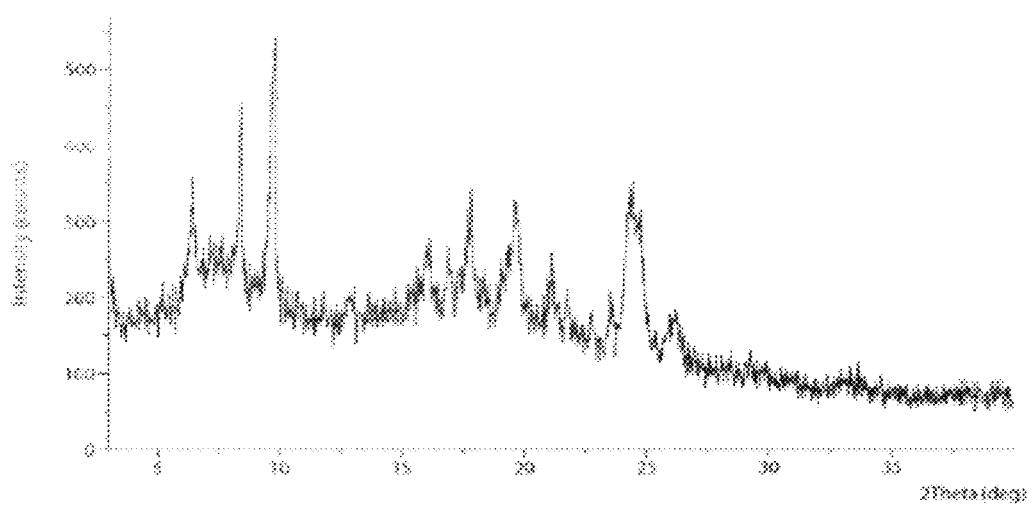
FIG. 5 is an X-ray powder diffractogram (XPRD) of COMPOUND 1 form 5.

In one embodiment, a single crystalline form, Form 5, of COMPOUND 1 is characterized by the X-ray powder diffraction (XRPD) pattern shown in FIG. 5, and data shown in Table 5, obtained using CuKα radiation. In a particular embodiment, the polymorph can be characterized by one or more of the peaks taken from FIG. 5, as shown in Table 5.

For example, the polymorph can be characterized by one or two or three or four or five or six or seven or eight or nine of the peaks shown in Table 5.

TABLE 5

| Angle 2- | Intensity % |
|---|---|
| 6.4 | 45.4 |
| 8.4 | 84.0 |
| 9.8 | 100.0 |
| 16.1 | 26.0 |
| 16.9 | 22.7 |
| 17.8 | 43.6 |
| 19.7 | 40.4 |
| 21.1 | 20.5 |
| 26.1 | 15.9 |

In another embodiment, Form 5 can be characterized by the peaks identified at 2θ angles of 6.4, 8.4, 9.8, 17.8, and 19.7°. In another embodiment, Form 5 can be characterized by the peaks identified at 2θ angles of 8.4 and 9.8°.

Form 6

Figure 6:
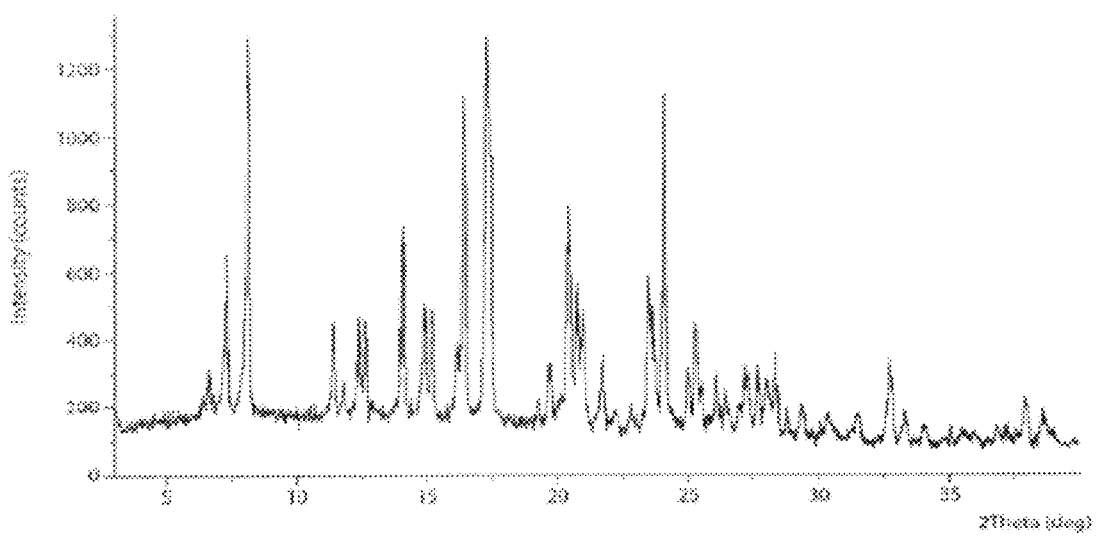
FIG. 6 is an X-ray powder diffractogram (XPRD) of COMPOUND 1 form 6.

In one embodiment, a single crystalline form, Form 6, of COMPOUND 1 is characterized by the X-ray powder diffraction (XRPD) pattern shown in FIG. 15, and data shown in Table 6, obtained using CuKα radiation. In a particular embodiment, the polymorph can be characterized by one or more of the peaks taken from FIG. 6, as shown in Table 6. For example, the polymorph can be characterized by one or two or three or four or five or six or seven or eight of the peaks shown in Table 6.

TABLE 6

| Angle 2- | Intensity % |
|---|---|
| 8.1 | 97.9 |
| 11.4 | 24.9 |
| 14.1 | 51.5 |
| 15.2 | 28.4 |
| 16.4 | 85.0 |
| 17.3 | 100.0 |
| 20.5 | 54.7 |
| 24.1 | 88.7 |

In another embodiment, Form 6 can be characterized by the peaks identified at 2θ angles of 8.1, 14.1, 16.4, 17.3, 20.5, and 24.1°. In another embodiment, Form 6 can be characterized by the peaks identified at 2θ angles of 8.1, 16.4, 17.3, and 24.1°.

RAS Targeting Compounds

In one embodiment, the methods provided herein comprise co-administration of one or more second agent, wherein the second agent is a RAS targeting agent. In one embodiment, the second agent targets KRAS, NRAS and/or HRAS.

In one aspect, the second agent targets the downstream components of the RAS signaling pathways, such as the Raf-MEK-ERK or PI3K-AKT-mTOR pathways. Exemplary second agents that target RAS oncogene are described by Takashima et al. in *Expert Opin Ther Targets.* 2013 May; 17(5): 507-531, incorporated by reference herein.

In one embodiment, the second agent is a Raf kinase inhibitor. In one embodiment, the second agent is a MEK kinase inhibitor. In one embodiment, the second agent is a ERK kinase inhibitor. In one embodiment, the second agent is a PI3K kinase inhibitor. In one embodiment, the second agent is a AKT kinase inhibitor. In one embodiment, the second agent is m-TOR kinase inhibitor.

In one embodiment, the second agent is a MEK kinase inhibitor. In one embodiment, the MEK kinase inhibitor is selected from trametinib (GSK1120212), selumetinib, binimetinib (MEK162), PD-325901, cobimetinib (XL518), CI-1040 and PD035901.

Compositions and Routes of Administration

In one embodiment, provided herein is a pharmaceutical composition comprising a therapeutically effective amount of a mutant IDH2 inhibitor. In one embodiment, the mutant IDH1 inhibitor is COMPOUND 1.

In one embodiment, the compounds utilized in the methods provided herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

Pharmaceutically acceptable carriers, adjuvants and vehicles that may be used in the pharmaceutical compositions of one aspect of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-3-cyclodextrins, or other solubilized derivatives may also be advantageously used to enhance delivery of COMPOUND 1 or COMPOUND 2 described herein.

In one embodiment, the pharmaceutical composition comprises COMPOUND 1 and an excipient. In one embodiment, the pharmaceutical composition that comprises COMPOUND 1 and an excipient, is for oral administration. In one embodiment, the excipient is a diluent, a binder, a disintegrant, a wetting agent, a stabilizer, a glidant, or a lubricant.

In one embodiment, the diluent is a microcrystalline cellulose.

In one embodiment, the binder is a hydroxypropyl cellulose.

In one embodiment, the disintegrant is sodium starch glycolate.

In one embodiment, the wetting agent is sodium lauryl sulfate.

In one embodiment, the stabilizer is hypromellose acetate succinate.

In one embodiment, the glidant is colloidal silicon dioxide.

In one embodiment, the lubricant is magnesium stearate.

In one embodiment, the pharmaceutical composition comprises COMPOUND 1 or COMPOUND 2 and an excipient. In one embodiment, the pharmaceutical composition that comprises COMPOUND 1 or COMPOUND 2 and an excipient, is for oral administration.

Oral delivery formats for COMPOUND 1 or COMPOUND 2 include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains COMPOUND 1 or COMPOUND 2.

Particular embodiments herein provide solid oral dosage forms that are tablets or capsules. In certain embodiments, the formulation is a tablet comprising COMPOUND 1 or COMPOUND 2. In certain embodiments, the formulation is a capsule comprising COMPOUND 1 or COMPOUND 2. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the active pharmaceutical ingredient (API), e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. In certain embodiments, embodiments herein encompass the use of COMPOUND 1 for the preparation of a pharmaceutical composition for treating a malignancy, characterized by the presence of a mutant allele of IDH2, wherein the composition is prepared for oral administration. In certain embodiments, embodiments herein encompass the use of COMPOUND 2 for the preparation of a pharmaceutical composition for treating a malignancy, characterized by the presence of a mutant allele of IDH1, wherein the composition is prepared for oral administration.

Particular embodiments herein provide pharmaceutical formulations (e.g., immediate release oral formulations and/or formulations that release the API substantially in the stomach) comprising COMPOUND 1 or COMPOUND 2 that achieve a particular AUC value (e.g., AUC(0-t) or AUC(0-∞)) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, or at least about 2500 ng-hr/mL. In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release the API substantially in the stomach) comprising COMPOUND 1 or COMPOUND 2 that achieve a particular maximum plasma concentration ("Cmax") in the subject to which the formulation is orally administered. Particular embodiments provide oral formulations that achieve a Cmax of COMPOUND 1 or COMPOUND 2 of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL.

Particular embodiments herein provide pharmaceutical formulations (e.g., immediate release oral formulations and/or formulations that release the API substantially in the stomach) comprising COMPOUND 1 or COMPOUND 2 that achieve a particular time to maximum plasma concentration ("Tmax") in the subject to which the formulation is orally administered. Particular embodiments provide oral formulations that achieve a Tmax of the cytidine analog of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising COMPOUND 1 or COMPOUND 2 wherein the oral dosage forms have an enteric coating. Particular embodiments provide a permeable or partly permeable (e.g., "leaky") enteric coating with pores. In particular embodiments, the permeable or partly permeable enteric-coated tablet releases COMPOUND 1 or COMPOUND 2 in an immediate release manner substantially in the stomach.

Provided herein are dosage forms designed to maximize the absorption and/or efficacious delivery of COMPOUND 1 or COMPOUND 2, upon oral administration, e.g., for release substantially in the stomach. Accordingly, certain embodiments herein provide a solid oral dosage form of COMPOUND 1 or COMPOUND 2 using pharmaceutical excipients designed for immediate release of the API upon oral administration, e.g., substantially in the stomach. Particular immediate release formulations comprise a specific amount of COMPOUND 1 or COMPOUND 2 and optionally one or more excipients. In certain embodiments, the formulation may be an immediate release tablet or an immediate release capsule (such as, e.g., an HPMC capsule).

Provided herein are methods of making the formulations provided herein comprising COMPOUND 1 or COMPOUND 2 provided herein (e.g., immediate release oral formulations and/or formulations that release the API substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., immediate release oral formulations, formulations that release the API substantially in the stomach, or rapidly disintegrating formulations that dissolve substantially in the mouth) comprise COMPOUND 1 or COMPOUND 2 in a specific amount. In particular embodiments, the specific amount of COMPOUND 1 or COMPOUND 2 in the formulation is, e.g., about 10 mg. In one embodiment, the specific amount is about 20 mg. In one embodiment, the specific amount is about 40 mg. In one embodiment, the specific amount is about 60 mg. In one embodiment, the specific amount is about 80 mg. In one embodiment, the specific amount is about 100 mg. In one embodiment, the specific amount is about 120 mg. In one embodiment, the specific amount is about 140 mg. In one embodiment, the specific amount is about 160 mg. In one embodiment, the specific amount is about 180 mg. In one embodiment, the specific amount is about 200 mg. In one embodiment, the specific amount is about 220 mg. In one embodiment, the specific amount is about 240 mg. In one embodiment, the specific amount is about 260 mg. In one embodiment, the specific amount is about 280 mg. In one embodiment, the specific amount is about 300 mg. In one embodiment, the specific amount is about 320 mg. In one embodiment, the specific amount is about 340 mg. In one embodiment, the specific amount is about 360 mg. In one embodiment, the specific amount is about 380 mg. In one embodiment, the specific amount is about 400 mg. In one embodiment, the specific amount is about 420 mg. In one embodiment, the specific amount is about 440 mg. In one embodiment, the specific amount is about 460 mg. In one embodiment, the specific amount is about 480 mg. In one embodiment, the specific amount is about 500 mg. In one embodiment, the specific amount is about 600 mg. In one embodiment, the specific amount is about 700 mg. In one embodiment, the specific amount is about 800 mg. In one embodiment, the specific amount is about 900 mg. In one embodiment, the specific amount is about 1000 mg. In one embodiment, the specific amount is about 1100 mg. In one embodiment, the specific amount is about 1200 mg. In one embodiment, the specific amount is about 1300 mg. In one embodiment, the specific amount is about 1400 mg. In one embodiment, the specific amount is about 1500 mg. In one embodiment, the specific amount is about 1600 mg. In one embodiment, the specific amount is about 1700 mg. In one embodiment, the specific amount is about 1800 mg. In one embodiment, the specific amount is about 1900 mg. In one embodiment, the specific amount is about 2000 mg. In one embodiment, the specific amount is about 2100 mg. In one embodiment, the specific amount is about 2200 mg. In one embodiment, the specific amount is about 2300 mg. In one embodiment, the specific amount is about 2400 mg. In one embodiment, the specific amount is about 2500 mg. In one embodiment, the specific amount is about 3000 mg. In one embodiment, the specific amount is about 4000 mg. In one embodiment, the specific amount is about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising COMPOUND 1 or COMPOUND 2 alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of COMPOUND 1 or COMPOUND 2 and vegetable oil or non-aqueous, water miscible materials such as, for example, polyethylene glycol and the like. In certain embodiments, hard gelatin capsules may be prepared containing granules of COMPOUND 1 or COMPOUND 2 in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of COMPOUND 1 or COMPOUND 2 is prepared using aqueous solvents without causing significant hydrolytic degradation of the compounds. In particular embodiments, the formulation of COMPOUND 1 or COMPOUND 2 is a tablet which contains a coating applied to the drug core using aqueous solvents without causing significant hydrolytic degradation of the compound in the formulation. In certain embodiments, water is employed as the solvent for coating the drug core. In certain embodiments, the oral dosage form of COMPOUND 1 or COMPOUND 2 is a tablet containing a film coat applied to the drug core using aqueous solvents. In particular embodiments, water is employed as the solvent for film-coating. In particular embodiments, the tablet containing COMPOUND 1 or COMPOUND 2 is film-coated using aqueous solvents without effecting degradation of the pharmaceutical composition. In particular embodiments, water is used as the film coating solvent without effecting degradation of the pharmaceutical composition. In certain embodiments, an oral dosage form comprising COMPOUND 1 or COMPOUND 2 and an aqueous film coating effects immediate drug release upon oral delivery. In certain embodiments, the oral dosage form comprising COMPOUND 1 or COMPOUND 2 and an aqueous film coating effects controlled drug release to the upper gastrointestinal tract, e.g., the stomach, upon oral administration. In particular embodiments, a tablet with an aqueous-based film coating comprises COMPOUND 1 or COMPOUND 2 as the API.

In certain embodiments, provided herein is a controlled release pharmaceutical formulation for oral administration of COMPOUND 1 or COMPOUND 2 substantially in the stomach, comprising: a) a specific amount of COMPOUND 1 or COMPOUND 2; b) a drug release controlling component for controlling the release of COMPOUND 1 or COMPOUND 2 substantially in the upper gastrointestinal tract, e.g., the stomach; and c) optionally one or more excipients. In certain embodiments, the oral dosage form comprising COMPOUND 1 or COMPOUND 2 is prepared as a controlled release tablet or capsule which includes a drug core comprising the pharmaceutical composition and optional excipients. Optionally, a "seal coat" or "shell" is applied. In certain embodiments, a formulation provided herein comprising COMPOUND 1 or COMPOUND 2 provided herein is a controlled release tablet or capsule, which comprises a therapeutically effective amount of COMPOUND 1 or COMPOUND 2, a drug release controlling component that controls the release of COMPOUND 1 or COMPOUND 2 substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of COMPOUND 1 or COMPOUND 2 from the polymer matrix substantially in the stomach. In certain embodiments, such formulations may be prepared by incorporating COMPOUND 1 or COMPOUND 2 into a suitable polymeric matrix during formulation. Examples of such formulations are known in the art. See, e.g., Shell et al., U.S. Patent Publication No. 2002/0051820 (application Ser. No. 09/990,061); Shell et al., U.S. Patent Publication No. 2003/0039688 (application Ser. No. 10/045, 823); Gusler et al., U.S. Patent Publication No. 2003/ 0104053 (application Ser. No. 10/029,134), each of which is incorporated herein by reference in its entirety.

In certain embodiments, the drug release controlling component may comprise a shell surrounding the drug-containing core, wherein the shell releases COMPOUND 1 or COMPOUND 2 from the core by, e.g., permitting diffusion of COMPOUND 1 or COMPOUND 2 from the core and promoting gastric retention of the formulation by swelling upon exposure to gastric fluids to a size that is retained in the stomach. In certain embodiments, such formulations may be prepared by first compressing a mixture of COMPOUND 1 or COMPOUND 2 and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

In certain embodiments, the pharmaceutical formulations provided herein contain COMPOUND 1 or COMPOUND 2 and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, *ceratonia*, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% ore more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of *theobroma*, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or cross-linked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-Alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, *ceratonia*, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sufobutyl-b-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In one embodiment, the pharmaceutical compositions provided herein may be administered orally, parenterally, by inhalation spray, topically, rectally, nasally, buccally, vaginally or via an implanted reservoir, preferably by oral administration or administration by injection. In one embodiment, the pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In one embodiment, the pharmaceutical compositions provided herein may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In one embodiment, the pharmaceutical compositions provided herein may also be administered in the form of suppositories for rectal administration. These compositions can be prepared by mixing a compound of one aspect of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herein is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herein may also be topically applied to the lower intestinal tract by rectal suppository formulation or in a suitable enema formulation. Topically-transdermal patches are also included herein.

In one embodiment, the pharmaceutical compositions provided herein may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In one embodiment, the compositions provided herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. In one embodiment, the pharmaceutical compositions are administered from about 1 to about 6 times per day or alternatively, as a continuous infusion. Such administration can be used as a chronic or acute therapy. The amount of active ingredient that may be combined with the carrier materials to produce a single dosage form varies depending upon the host treated and the particular mode of administration. A typical preparation contains from about 5% to about 95% active compound (w/w). Alternatively, such preparations contain from about 20% to about 80% active compound.

Lower or higher doses than those recited above may be required. Specific dosage and treatment regimens for any particular subject depends upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination provided herein may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Use

It has been observed that the mutation status of NRAS oncogene is associated with responses in cancer characterized by the presence of a mutant allele of IDH2 when treated with COMPOUND 1 and in cancer characterized by the presence of a mutant allele of IDH1 when treated with COMPOUND 2. While not intending to be bound by any particular theory of operation, somatic mutations in NRAS oncogene may be associated with resistance to treatment with COMPOUND 1 in AML characterized by the presence of a mutant allele of IDH2, and resistance to treatment with COMPOUND 2 in AML characterized by the presence of a mutant allele of IDH1.

In certain embodiments, an NRAS mutation at one or more sites selected from G12, G13 and Q61 may be associated with resistance to treatment with COMPOUND 1 in a cancer characterized by the presence of a mutant allele of IDH2.

In certain embodiments, an NRAS mutation co-occurring with 6 or more other mutations, may be associated with resistance to treatment with COMPOUND 1 in a cancer characterized by the presence of a mutant allele of IDH2. In certain embodiments, an NRAS mutation at one or more sites selected from G12, G13 and Q61 co-occurring with 6 or more other mutations, may be associated with resistance to treatment with COMPOUND 1 in a cancer characterized by the presence of a mutant allele of IDH2.

In certain embodiments, an NRAS mutation at one or more sites selected from G12, G13 and Q61 may be associated with resistance to treatment with COMPOUND 1 in AML characterized by the presence of a mutant allele of IDH2.

In certain embodiments, an NRAS mutation co-occurring with 6 or more other mutations, may be associated with resistance to treatment with COMPOUND 1 in AML characterized by the presence of a mutant allele of IDH2. In certain embodiments, an NRAS mutation at one or more sites selected from G12, G13 and Q61 co-occurring with 6 or more other mutations, may be associated with resistance to treatment with COMPOUND 1 in AML characterized by the presence of a mutant allele of IDH2.

In one embodiment, the methods provided herein encompass treating, preventing, or managing cancer in a subject, wherein the cancer is characterized by the presence of a mutant allele of IDH2 and the absence of a mutant allele of NRAS, by administering a therapeutically effective amount of an IDH2 inhibitor. In one embodiment, the IDH2 inhibitor is COMPOUND 1. In certain embodiments, the cancer is relapsed or refractory.

In one embodiment, the methods provided herein encompass treating, preventing, or managing cancer in a subject, wherein the cancer is characterized by the presence of a mutant allele of IDH2 and the absence of an NRAS mutation at G12, G13 or Q61, by administering a therapeutically effective amount of an IDH2 inhibitor. In one embodiment, the IDH2 inhibitor is COMPOUND 1. In certain embodiments, the cancer is relapsed or refractory.

In one embodiment, the methods provided herein encompass treating, preventing, or managing cancer in a subject, wherein the cancer is characterized by the presence of a mutant allele of IDH2, the absence of a mutant allele of NRAS and having 3 or less co-occurring mutations, by administering a therapeutically effective amount of an IDH2 inhibitor. In one embodiment, the IDH2 inhibitor is COMPOUND 1. In certain embodiments, the cancer is relapsed or refractory.

In one embodiment, the methods provided herein encompass treating, preventing, or managing cancer in a subject, wherein the cancer is characterized by the presence of a mutant allele of IDH2, the absence of an NRAS mutation at one or more sites selected from G12, G13 and Q61 and having 3 or less co-occurring mutations, by administering a therapeutically effective amount of an IDH2 inhibitor. In one embodiment, the IDH2 inhibitor is COMPOUND 1. In certain embodiments, the cancer is relapsed or refractory.

In one embodiment, provided herein is a method of treating, preventing, or managing solid tumors in a subject, wherein the solid tumor is characterized by the presence of a mutant allele of IDH2 and the absence of a mutant allele of NRAS by administering a therapeutically effective amount of COMPOUND 1. In one embodiment, the solid tumor is an advanced solid tumor.

In one embodiment, the methods provided herein encompass treating, preventing, or managing a solid tumor in a subject, wherein the cancer is characterized by the presence of a mutant allele of IDH2 and the absence of an NRAS mutation at G12, G13 or Q61, by administering a therapeutically effective amount of an IDH2 inhibitor. In one embodiment, the IDH2 inhibitor is COMPOUND 1. In one embodiment, the solid tumor is an advanced solid tumor.

In one embodiment, the methods provided herein encompass treating, preventing, or managing a solid tumor in a subject, wherein the cancer is characterized by the presence of a mutant allele of IDH2, the absence of a mutant allele of NRAS and having 3 or less co-occurring mutations, by administering a therapeutically effective amount of an IDH2 inhibitor. In one embodiment, the IDH2 inhibitor is COMPOUND 1. In one embodiment, the solid tumor is an advanced solid tumor.

In one embodiment, the methods provided herein encompass treating, preventing, or managing a solid tumor in a subject, wherein the cancer is characterized by the presence of a mutant allele of IDH2, the absence of an NRAS mutation at one or more sites selected from G12, G13 and Q61 and having 3 or less co-occurring mutations, by administering a therapeutically effective amount of an IDH2 inhibitor. In one embodiment, the IDH2 inhibitor is COMPOUND 1. In one embodiment, the solid tumor is an advanced solid tumor.

In one embodiment, provided herein is a method of treating, preventing, or managing hematological malignancies in a subject, wherein the hematological malignancy is characterized by the presence of a mutant allele of IDH2 and the absence of a mutant allele of NRAS by administering a therapeutically effective amount of COMPOUND 1. In one embodiment, the hematologic malignancy is an advanced hematologic malignancy. In certain embodiments, the hematologic malignancy is relapsed or refractory.

In one embodiment, the methods provided herein encompass treating, preventing, or managing hematological malignancies in a subject, wherein the cancer is characterized by the presence of a mutant allele of IDH2 and the absence of an NRAS mutation at G12, G13 or Q61, by administering a therapeutically effective amount of an IDH2 inhibitor. In one embodiment, the IDH2 inhibitor is COMPOUND 1. In one embodiment, the hematologic malignancy is an advanced hematologic malignancy. In certain embodiments, the hematologic malignancy is relapsed or refractory.

In one embodiment, the methods provided herein encompass treating, preventing, or managing hematological malignancies in a subject, wherein the cancer is characterized by the presence of a mutant allele of IDH2, the absence of a mutant allele of NRAS and having 3 or less co-occurring mutations, by administering a therapeutically effective amount of an IDH2 inhibitor. In one embodiment, the IDH2 inhibitor is COMPOUND 1. In one embodiment, the hematologic malignancy is an advanced hematologic malignancy. In certain embodiments, the hematologic malignancy is relapsed or refractory.

In one embodiment, the methods provided herein encompass treating, preventing, or managing hematological malignancies in a subject, wherein the cancer is characterized by the presence of a mutant allele of IDH2, the absence of an NRAS mutation at one or more sites selected from G12, G13 and Q61 and having 3 or less co-occurring mutations, by administering a therapeutically effective amount of an IDH2 inhibitor. In one embodiment, the IDH2 inhibitor is COMPOUND 1. In one embodiment, the hematologic malignancy is an advanced hematologic malignancy. In certain embodiments, the hematologic malignancy is relapsed or refractory.

In certain embodiments, the methods encompass treating, preventing, or managing cancer in a subject, wherein the cancer is characterized by the presence of a mutant allele of IDH2 and a mutant allele of NRAS by administering a therapeutically effective amount of an IDH2 inhibitor, such as COMPOUND 1 in combination with a therapeutically effective amount of one or more compounds that target the RAS pathway. In one embodiment, the compound that targets the RAS pathway is a MEK kinase inhibitor compound. In one embodiment, the MEK kinase inhibitor is selected from trametinib, selumetinib, binimetinib, PD-325901, cobimetinib, CI-1040 and PD035901.

In certain embodiments, the methods encompass treating, preventing, or managing a solid tumor in a subject, wherein the solid tumor is characterized by the presence of a mutant allele of IDH2 and a mutant allele of NRAS by administering a therapeutically effective amount of an IDH2 inhibitor, such as COMPOUND 1 in combination with a therapeutically effective amount of one or more compounds that the target RAS pathway. In one embodiment, the compound that targets the RAS pathway is a MEK kinase inhibitor compound. In one embodiment, the MEK kinase inhibitor is selected from trametinib, selumetinib, binimetinib, PD-325901, cobimetinib, CI-1040 and PD035901.

In one embodiment, the solid tumor is an advanced solid tumor.

In certain embodiments, the methods encompass treating, preventing, or managing a hematologic malignancy in a subject, wherein the hematological malignancy is characterized by the presence of a mutant allele of IDH2 and a mutant allele of NRAS by administering a therapeutically effective amount of an IDH2 inhibitor, such as COMPOUND 1 in combination with a therapeutically effective amount of one or more compounds that target the RAS pathway. In one embodiment, the compound that targets the RAS pathway is a MEK kinase inhibitor compound. In one embodiment, the MEK kinase inhibitor is selected from trametinib, selumetinib, binimetinib, PD-325901, cobimetinib, CI-1040 and PD035901.

In one embodiment, the hematologic malignancy is an advanced hematologic malignancy.

In certain embodiments, methods provided herein comprise contacting a cancer cell in or from a subject, such as a patient, wherein the cancer cell is characterized by the presence of a mutant allele of IDH2 and the absence of a mutant allele of NRAS, with a therapeutically effective amount of COMPOUND 1. The contacting can be in vitro, in vivo, or ex vivo. In one embodiment, the method comprises contacting the cancer cell in vivo.

In one embodiment, provided herein is a method of identifying a cancer subject suitable for treatment with an IDH2 inhibitor, comprising: (a) obtaining a biological sample from a subject having cancer; (b) screening the biological sample for a mutant allele of IDH2 and a mutant allele of NRAS; and (c) if the cancer is characterized by the presence of a mutant allele of IDH2 and the absence of a mutant allele of NRAS, identifying the subject as a cancer subject suitable for treatment with an IDH2 inhibitor. In another embodiment, the subjects identified as cancer subjects suitable for treatment with an IDH2 inhibitor are treated with an IDH2 inhibitor.

In one embodiment, provided is an IDH2 inhibitor for use in a method for treating cancer in a cancer subject, wherein the cancer subject has been identified by the method of identifying the cancer subject suitable for treatment with an IDH2 inhibitor, comprising: (a) obtaining a biological sample from a subject having cancer; (b) screening the biological sample for a mutant allele of IDH2 and a mutant allele of NRAS; and (c) if the cancer is characterized by the presence of a mutant allele of IDH2 and the absence of a mutant allele of NRAS, identifying the subject as a cancer subject suitable for treatment with an IDH2 inhibitor.

Provided is also an IDH2 inhibitor for use in a method for treating cancer in a cancer subject, wherein the cancer subject has been identified by the method of identifying a cancer subject suitable for treatment with an IDH2 inhibitor, comprising: (a) obtaining a biological sample from a subject having cancer; (b) screening the biological sample for a mutant allele of IDH2 and a mutant allele of NRAS; and (c) if the cancer is characterized by the presence of a mutant allele of IDH2 and the absence of a mutant allele of NRAS, identifying the subject as a cancer subject suitable for treatment with an IDH2 inhibitor.

In one embodiment, provided herein is a method of identifying a cancer subject suitable for treatment with COMPOUND 1, comprising: (a) obtaining a biological sample from a subject having cancer; (b) screening the biological sample for a mutant allele of IDH2 and a mutant allele of NRAS; and (c) if the cancer is characterized by the presence of a mutant allele of IDH2 and the absence of a mutant allele of NRAS, identifying the subject as a cancer subject suitable for treatment with COMPOUND 1. In another embodiment, the subjects identified as cancer subjects suitable for treatment with COMPOUND 1 are treated with COMPOUND 1.

Provided is also COMPOUND 1 for use in a method for treating cancer in a cancer subject, wherein the cancer subject has been identified by the method of identifying a cancer subject suitable for treatment with COMPOUND 1, comprising: (a) obtaining a biological sample from a subject having cancer; (b) screening the biological sample for a mutant allele of IDH2 and a mutant allele of NRAS; and (c) if the cancer is characterized by the presence of a mutant allele of IDH2 and the absence of a mutant allele of NRAS, identifying the subject as a cancer subject suitable for treatment with COMPOUND 1.

In another embodiment, provided herein is a method for identifying one or more cancer subjects suitable for treatment with an IDH2 inhibitor from a plurality of cancer subjects with a cancer characterized by the presence of a mutant allele of IDH2. The method comprises identifying one or more cancer subjects with a cancer characterized by the absence of a mutant allele of NRAS from the plurality of cancer subjects suitable for treatment with an IDH2 inhibitor. In one embodiment, one or more suitable subjects are treated with an IDH2 inhibitor.

Provided is also the IDH2 inhibitor for use in a method for treating cancer in one or more cancer subjects with a cancer characterized by the presence of a mutant allele of IDH2, wherein the one or more cancer subjects are identified by the method comprising identifying one or more cancer subjects with a cancer characterized by the absence of a mutant allele of NRAS from the plurality of cancer subjects suitable for treatment with an IDH2 inhibitor.

In another embodiment, provided herein is a method for identifying one or more cancer subjects suitable for treatment with COMPOUND 1 from a plurality of cancer subjects, with a cancer characterized by the presence of a mutant allele of IDH2. The method comprises identifying one or more cancer subjects with a cancer characterized by the absence of a mutant allele of NRAS from the plurality of cancer subjects suitable for treatment with COMPOUND 1. In one embodiment, one or more suitable subjects are treated with COMPOUND 1.

Provided is also COMPOUND 1 for use in a method for treating cancer in one or more cancer subjects with a cancer characterized by the presence of a mutant allele of IDH2, wherein the one or more cancer subjects are identified by the method comprising identifying one or more cancer subjects with a cancer characterized by the absence of a mutant allele of NRAS from the plurality of cancer subjects suitable for treatment with COMPOUND 1.

In one embodiment, the RAS pathway inhibitor is a MEK kinase inhibitor selected from trametinib, selumetinib, binimetinib, PD-325901, cobimetinib, CI-1040 and PD035901.

In one embodiment, provided herein is a method of identifying a cancer subject suitable for treatment with a combination of an IDH2 inhibitor and a RAS pathway inhibitor, comprising: (a) obtaining a biological sample from a subject having cancer; (b) screening the biological sample for a mutant allele of IDH2 and a NRAS mutation; and (c) if the cancer is characterized by the presence of a mutant allele of IDH2 and a mutant allele of NRAS, identifying the subject as a cancer subject suitable for treatment with a combination therapy with an IDH2 inhibitor and a RAS pathway inhibitor. In another embodiment, the subjects identified as cancer subjects suitable for treatment with the combination therapy are treated with a combination of an IDH2 inhibitor and a RAS pathway inhibitor.

Provided is also a combination of an IDH2 inhibitor and a RAS pathway inhibitor for use in a method for treating cancer in a cancer subject, wherein the cancer subject has been identified by the method of identifying a cancer subject suitable for treatment with a combination of an IDH2 inhibitor and a RAS pathway inhibitor, comprising: (a) obtaining a biological sample from a subject having cancer; (b) screening the biological sample for a mutant allele of IDH2 and a NRAS mutation; and (c) if the cancer is characterized by the presence of a mutant allele of IDH2 and a mutant allele of NRAS, identifying the subject as a cancer subject suitable for treatment with a combination therapy with an IDH2 inhibitor and a RAS pathway inhibitor.

In one embodiment, the RAS pathway inhibitor is a MEK kinase inhibitor selected from trametinib, selumetinib, binimetinib, PD-325901, cobimetinib, CI-1040 and PD035901.

In one embodiment, provided herein is a method of identifying a cancer subject suitable for treatment with a combination of COMPOUND 1 and a RAS pathway inhibitor, comprising: (a) obtaining a biological sample from a subject having cancer; (b) screening the biological sample for a mutant allele of IDH2 and a NRAS mutation; and (c) if the cancer is characterized by the presence of a mutant allele of IDH2 and a mutant allele of NRAS, identifying the subject as a cancer subject suitable for treatment with a combination therapy with COMPOUND 1 and a RAS pathway inhibitor. In another embodiment, the subjects identified as cancer subjects suitable for treatment with the combination therapy are treated with a combination of COMPOUND 1 and a RAS pathway inhibitor. In one embodiment, the RAS pathway inhibitor is selected from trametinib, selumetinib, binimetinib, PD-325901, cobimetinib, CI-1040 and PD035901.

In another embodiment, provided herein is a method for identifying one or more cancer subjects suitable for treatment with a combination therapy with an IDH2 inhibitor, for example COMPOUND 1, and RAS pathway inhibitor, for example, trametinib, selumetinib, binimetinib, PD-325901, cobimetinib, CI-1040 or PD035901, from a plurality of cancer subjects. The method comprises identifying one or more cancer subjects, wherein the cancer is characterized by the presence of a mutant allele of IDH2 and a mutant allele of NRAS from the plurality of cancer subjects suitable for treatment with a combination therapy with an IDH2 inhibitor, for example COMPOUND 1, and RAS pathway inhibitor, for example, trametinib, selumetinib, binimetinib, PD-325901, cobimetinib, CI-1040 or PD035901. In one embodiment, one or more suitable subjects are treated with a combination of an IDH2 inhibitor, for example COMPOUND 1, and RAS pathway inhibitor, for example, trametinib, selumetinib, binimetinib, PD-325901, cobimetinib, CI-1040 or PD035901.

Provided is also a combination of an IDH2 inhibitor, for example COMPOUND 1, and RAS pathway inhibitor, for example, trametinib, selumetinib, binimetinib, PD-325901, cobimetinib, CI-1040 or PD035901 for use in a method for treating cancer in one or more cancer subjects, wherein the one or more cancer subjects are identified by the method comprising identifying one or more cancer subjects, wherein the cancer is characterized by the presence of a mutant allele of IDH2 and a mutant allele of NRAS from the plurality of cancer subjects suitable for treatment with a combination therapy with an IDH2 inhibitor, for example COMPOUND 1, and RAS pathway inhibitor, for example, trametinib, selumetinib, binimetinib, PD-325901, cobimetinib, CI-1040 or PD035901.

In some embodiments of the methods described herein, the hematologic malignancy is acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2. In some embodiments of the methods described herein, the hematologic malignancy is acute myelogenous leukemia (AML) characterized by the presence of a mutant allele of IDH2. In some embodiments of the methods described herein, the acute myelogenous leukemia (AML) is relapsed or refractory AML, characterized by the presence of a mutant allele of IDH2. In some embodiments of the methods described herein, the hematologic malignancy is myelodysplastic syndrome (MDS) characterized by the presence of a mutant allele of IDH2. In some embodiments of the methods described herein, the hematologic malignancy is chronic myelomonocytic leukemia (CMML) characterized by the presence of a mutant allele of IDH2. In some embodiments of the methods described herein, the hematologic malignancy is myeloid sarcoma characterized by the presence of a mutant allele of IDH2. In some embodiments of the methods described herein, the hematologic malignancy is lymphoma (e.g., T-cell lymphoma or B-cell lymphoma) characterized by the presence of a mutant allele of IDH2. In some embodiments of the methods described herein, the hematologic malignancy is angioimmunoblastic T-cell lymphoma (AITL) characterized by the presence of a mutant allele of IDH2. In some embodiments of the methods described herein, the hematologic malignancy is blastic plasmacytoid dendritic cell neoplasm characterized by the presence of a mutant allele of IDH2.

In one embodiment of the methods provided herein the solid tumor is glioma, melanoma, chondrosarcoma, cholangiocarcinoma (e.g., glioma), angioimmunoblastic T-cell lymphoma (AITL), sarcoma, or non small cell lung cancer, each characterized by the presence of a mutant allele of IDH2. In one embodiment of the methods provided herein the solid tumor is glioma, characterized by the presence of a mutant allele of IDH2. In one embodiment of the methods provided herein the solid tumor is melanoma characterized by the presence of a mutant allele of IDH2. In one embodiment of the methods provided herein the solid tumor chondrosarcoma characterized by the presence of a mutant allele of IDH2. In one embodiment of the methods provided herein the solid tumor is cholangiocarcinoma (e.g., glioma) characterized by the presence of a mutant allele of IDH2. In one embodiment of the methods provided herein the solid tumor is angioimmunoblastic T-cell lymphoma (AITL) characterized by the presence of a mutant allele of IDH2. In one embodiment of the methods provided herein the solid tumor is sarcoma characterized by the presence of a mutant allele of IDH2. In one embodiment of the methods provided herein the solid tumor is non small cell lung cancer characterized by the presence of a mutant allele of IDH2.

In one embodiment of the methods provided herein the solid tumor is glioma, melanoma, chondrosarcoma, cholangiocarcinoma (including intrahepatic cholangiocarcinoma (IHCC), prostate cancer, colon cancer, or non-small cell lung cancer (NSCLC), each characterized by the presence of a mutant allele of IDH1.

In one embodiment, the malignancy to be treated is characterized by a mutant allele of IDH1 or IDH2, wherein the IDH1 or IDH2 mutation results in a new ability of the enzyme to catalyze the NADPH-dependent reduction of a ketoglutarate to R( ) 2 hydroxyglutarate in a patient. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

In another aspect, without being bound by theory, applicants have found that mutant alleles of IDH2, wherein the IDH2 mutation results in a new ability of the enzyme to catalyze the NADPH-dependent reduction of α ketoglutarate to R( ) 2 hydroxyglutarate, and in particular R140Q and/or R172K mutations of IDH2, characterize a subset of all types of cancers, without regard to their cellular nature or location in the body. Thus, the compounds, compositions and methods provided herein are useful to treat any type of cancer that is characterized by the presence of a mutant allele of IDH2 imparting such activity and in particular an IDH2 R140Q and/or R172K mutation.

Thus, COMPOUND 1, and methods described herein are useful to treat an hematologic malignancy, including an advanced hematologic malignancy, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 imparting such activity and in particular an IDH2 R140Q and/or R172K mutation.

In another aspect, COMPOUND 1 and methods described herein are useful to treat a solid tumor, such as glioma, melanoma, chondrosarcoma, cholangiocarcinoma (e.g., glioma), angioimmunoblastic T-cell lymphoma (AITL), sarcoma, or non small cell lung cancer, each characterized by the presence of a mutant allele of IDH 2 imparting such activity and in particular IDH2 R140Q and/or R172K mutation.

In one embodiment the malignancy is a tumor wherein at least 30, 40, 50, 60, 70, 80 or 90% of the tumor cells carry an IDH1 mutation, and in particular an an IDH1 R132H or R132C mutation, or an IDH2 mutation, and in particular an IDH2 R140Q, R140W, or R140L and/or R172K or R172G mutation, at the time of diagnosis or treatment.

In one embodiment, the efficacy of treatment of malignancy is monitored by measuring the levels of 2HG in the subject. Typically levels of 2HG are measured prior to treatment, wherein an elevated level is indicated for the use of COMPOUND 1 or COMPOUND 2. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, 2HG measurements are utilized together with other well-known determinations of efficacy of malignancy treatment, such as reduction in number and size of tumors and/or other cancer-associated lesions, improvement in the general health of the subject, and alterations in other biomarkers that are associated with malignancy treatment efficacy.

2HG can be detected in a sample by the methods of PCT Publication No. WO 2011/050210 and US Publication No. US2012/0121515 hereby incorporated by reference in their entirety, or by analogous methods. In an exemplary method, 2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. *Nat Biotechnol* 26, 1179-86, 2008.

In one embodiment, 2HG is directly evaluated.

In another embodiment, a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

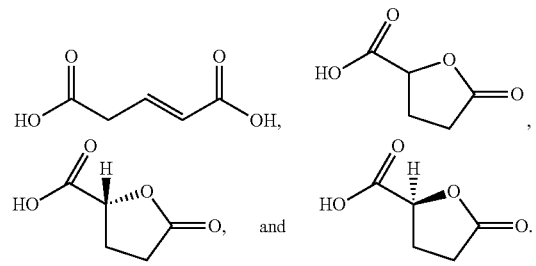

2HG is known to accumulate in the inherited metabolic disorder 2-hydroxyglutaric aciduria. This disease is caused by deficiency in the enzyme 2-hydroxyglutarate dehydrogenase, which converts 2HG to α-KG (Struys, E. A. et al. *Am J Hum Genet* 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, *J Neurooncol* 91, 233-6 (2009); Kolker, S., Mayatepek, E. & Hoffmann, G. F. *Neuropediatrics* 33, 225-31 (2002); Wajner, M., Latini, A., Wyse, A. T. & Dutra-Filho, C. S. *J Inherit Metab Dis* 27, 427-48 (2004)). Furthermore, elevated brain levels of 2HG result in increased ROS levels (Kolker, S. et al. *Eur J Neurosci* 16, 21-8 (2002); Latini, A. et al. *Eur J Neurosci* 17, 2017-22 (2003)), potentially contributing to an increased risk of cancer. The ability of 2HG to act as an NMDA receptor agonist may contribute to this effect (Kolker, S. et al. *Eur J Neurosci* 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hif1-alpha levels.

Treatment methods described herein can additionally comprise various evaluation steps prior to and/or following treatment with COMPOUND 1 or COMPOUND 2.

In one embodiment, prior to and/or after treatment with COMPOUND 1 or COMPOUND 2, alone or in combination with a RAS pathway inhibitor, the method further comprises the step of evaluating the growth, size, weight, invasiveness, stage and/or other phenotype of the malignancy.

In one embodiment, prior to and/or after treatment with COMPOUND 1, alone or in combination with a RAS pathway inhibitor, the method further comprises the step of evaluating the IDH2 genotype of the malignancy. This may be achieved by ordinary methods in the art, such as DNA sequencing, immuno analysis, and/or evaluation of the presence, distribution or level of 2HG. In one embodiment, prior to and/or after treatment with COMPOUND 2, alone or in combination with a RAS pathway inhibitor, the method further comprises the step of evaluating the IDH1 genotype of the malignancy. This may be achieved by ordinary methods in the art, such as DNA sequencing, immuno analysis, and/or evaluation of the presence, distribution or level of 2HG.

In one embodiment, prior to and/or after treatment with COMPOUND 1 or COMPOUND 2, alone or in combination with a RAS pathway inhibitor, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

In one embodiment, COMPOUND 1 and a RAS pathway inhibitor are administered concurrently. In one embodiment, COMPOUND 1 and a RAS pathway inhibitor are administered sequentially. In one embodiment, COMPOUND 2 and a RAS pathway inhibitor are administered concurrently. In one embodiment, COMPOUND 2 and a RAS pathway inhibitor are administered sequentially.

In one embodiment, depending on the disease to be treated and the subject's condition, COMPOUND 1 may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. COMPOUND 1 may be formulated alone or together with one or more active agent(s), in suitable dosage unit with pharmaceutically acceptable excipients, carriers, adjuvants and vehicles, appropriate for each route of administration.

In one embodiment, the amount of COMPOUND 1 or COMPOUND 2 administered in the methods provided herein may range, e.g., between about 5 mg/day and about 2,000 mg/day. In one embodiment, the range is between about 10 mg/day and about 2,000 mg/day. In one embodiment, the range is between about 20 mg/day and about 2,000 mg/day. In one embodiment, the range is between about 50 mg/day and about 1,000 mg/day. In one embodiment, the range is between about 100 mg/day and about 1,000 mg/day. In one embodiment, the range is between about 100 mg/day and about 500 mg/day. In one embodiment, the range is between about 150 mg/day and about 500 mg/day. In one embodiment, the range is or between about 150 mg/day and about 250 mg/day. In certain embodiments, particular dosages are, e.g., about 10 mg/day. In one embodiment, the dose is about 20 mg/day. In one embodiment, the dose is about 50 mg/day. In one embodiment, the dose is about 75 mg/day. In one embodiment, the dose is about 100 mg/day. In one embodiment, the dose is about 120 mg/day. In one embodiment, the dose is about 150 mg/day. In one embodiment, the dose is about 200 mg/day. In one embodiment, the dose is about 250 mg/day. In one embodiment, the dose is about 300 mg/day. In one embodiment, the dose is about 350 mg/day. In one embodiment, the dose is about 400 mg/day. In one embodiment, the dose is about 450 mg/day. In one embodiment, the dose is about 500 mg/day. In one embodiment, the dose is about 600 mg/day. In one embodiment, the dose is about 700 mg/day. In one embodiment, the dose is about 800 mg/day. In one embodiment, the dose is about 900 mg/day. In one embodiment, the dose is about 1,000 mg/day. In one embodiment, the dose is about 1,200 mg/day. In one embodiment, the dose is or about 1,500 mg/day. In certain embodiments, particular dosages are, e.g., up to about 10 mg/day. In one embodiment, the particular dose is up to about 20 mg/day. In one embodiment, the particular dose is up to about 50 mg/day. In one embodiment, the particular dose is up to about 75 mg/day. In one embodiment, the particular dose is up to about 100 mg/day. In one embodiment, the particular dose is up to about 120 mg/day. In one embodiment, the particular dose is up to about 150 mg/day. In one embodiment, the particular dose is up to about 200 mg/day. In one embodiment, the particular dose is up to about 250 mg/day. In one embodiment, the particular dose is up to about 300 mg/day. In one embodiment, the particular dose is up to about 350 mg/day. In one embodiment, the particular dose is up to about 400 mg/day. In one embodiment, the particular dose is up to about 450 mg/day. In one embodiment, the particular dose is up to about 500 mg/day. In one embodiment, the particular dose is up to about 600 mg/day. In one embodiment, the particular dose is up to about 700 mg/day. In one embodiment, the particular dose is up to about 800 mg/day. In one embodiment, the particular dose is up to about 900 mg/day. In one embodiment, the particular dose is up to about 1,000 mg/day. In one embodiment, the particular dose is up to about 1,200 mg/day. In one embodiment, the particular dose is up to about 1,500 mg/day.

In one embodiment, the amount of COMPOUND 1 or COMPOUND 2 in the pharmaceutical composition or dosage form provided herein may range, e.g., between about 5 mg and about 2,000 mg. In one embodiment, the range is between about 10 mg and about 2,000 mg. In one embodiment, the range is between about 20 mg and about 2,000 mg. In one embodiment, the range is between about 50 mg and about 1,000 mg. In one embodiment, the range is between about 50 mg and about 500 mg. In one embodiment, the range is between about 50 mg and about 250 mg. In one embodiment, the range is between about 100 mg and about 500 mg. In one embodiment, the range is between about 150 mg and about 500 mg. In one embodiment, the range is between about 150 mg and about 250 mg. In certain embodiments, particular amounts are, e.g., about 10 mg. In one embodiment, the particular amount is about 20 mg. In one embodiment, the particular amount is about 30 mg. In one embodiment, the particular amount is about 50 mg. In one embodiment, the particular amount is about 75 mg. In one embodiment, the particular amount is about 100 mg. In one embodiment, the particular amount is about 120 mg. In one embodiment, the particular amount is about 150 mg. In one embodiment, the particular amount is about 200 mg. In one embodiment, the particular amount is about 250 mg. In one embodiment, the particular amount is about 300 mg. In one embodiment, the particular amount is about 350 mg. In one embodiment, the particular amount is about 400 mg. In one embodiment, the particular amount is about 450 mg. In one embodiment, the particular amount is about 500 mg. In one embodiment, the particular amount is about 600 mg. In one embodiment, the particular amount is about 650 mg. In one embodiment, the particular amount is about 700 mg. In one embodiment, the particular amount is about 800 mg. In one embodiment, the particular amount is about 900 mg. In one embodiment, the particular amount is about 1,000 mg. In one embodiment, the particular amount is about 1,200 mg. In one embodiment, the particular amount is or about 1,500 mg. In certain embodiments, particular amounts are, e.g., up to about 10 mg. In one embodiment, the particular amount is up to about 20 mg. In one embodiment, the particular amount is up to about 50 mg. In one embodiment, the particular amount is up to about 75 mg. In one embodiment, the particular amount is up to about 100 mg. In one embodiment, the particular amount is up to about 120 mg. In one embodiment, the particular amount is up to about 150 mg. In one embodiment, the particular amount is up to about 200 mg. In one embodiment, the particular amount is up to about 250 mg. In one embodiment, the particular amount is up to about 300 mg. In one embodiment, the particular amount is up to about 350 mg. In one embodiment, the particular amount is up to about 400 mg. In one embodiment, the particular amount is up to about 450 mg. In one embodiment, the particular amount is up to about 500 mg. In one embodiment, the particular amount is up to about 600 mg. In one embodiment, the particular amount is up to about 700 mg. In one embodiment, the particular amount is up to about 800 mg. In one embodiment, the particular amount is up to about 900 mg. In one embodiment, the particular amount is up to about 1,000 mg. In one embodiment, the particular amount is up to about 1,200 mg. In one embodiment, the particular amount is up to about 1,500 mg.

In one embodiment, COMPOUND 1 or COMPOUND 2 can be delivered as a single dose such as, e.g., a single bolus injection, or oral tablets or pills; or over time such as, e.g., continuous infusion over time or divided bolus doses over time. In one embodiment, COMPOUND 1 can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In certain embodiments, COMPOUND 1 or COMPOUND 2 is administered to a patient in cycles (e.g., daily administration for one week, then a rest period with no administration for up to three weeks). Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, a method provided herein comprises administering COMPOUND 1 or COMPOUND 2 in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or greater than 40 cycles. In one embodiment, the median number of cycles administered in a group of patients is about 1. In one embodiment, the median number of cycles administered in a group of patients is about 2. In one embodiment, the median number of cycles administered in a group of patients is about 3. In one embodiment, the median number of cycles administered in a group of patients is about 4. In one embodiment, the median number of cycles administered in a group of patients is about 5. In one embodiment, the median number of cycles administered in a group of patients is about 6. In one embodiment, the median number of cycles administered in a group of patients is about 7. In one embodiment, the median number of cycles administered in a group of patients is about 8. In one embodiment, the median number of cycles administered in a group of patients is about 9. In one embodiment, the median number of cycles administered in a group of patients is about 10. In one embodiment, the median number of cycles administered in a group of patients is about 11. In one embodiment, the median number of cycles administered in a group of patients is about 12. In one embodiment, the median number of cycles administered in a group of patients is about 13. In one embodiment, the median number of cycles administered in a group of patients is about 14. In one embodiment, the median number of cycles administered in a group of patients is about 15. In one embodiment, the median number of cycles administered in a group of patients is about 16. In one embodiment, the median number of cycles administered in a group of patients is about 17. In one embodiment, the median number of cycles administered in a group of patients is about 18. In one embodiment, the median number of cycles administered in a group of patients is about 19. In one embodiment, the median number of cycles administered in a group of patients is about 20. In one embodiment, the median number of cycles administered in a group of patients is about 21. In one embodiment, the median number of cycles administered in a group of patients is about 22. In one embodiment, the median number of cycles administered in a group of patients is about 23. In one embodiment, the median number of cycles administered in a group of patients is about 24. In one embodiment, the median number of cycles administered in a group of patients is about 25. In one embodiment, the median number of cycles administered in a group of patients is about 26. In one embodiment, the median number of cycles administered in a group of patients is about 27. In one embodiment, the median number of cycles administered in a group of patients is about 28. In one embodiment, the median number of cycles administered in a group of patients is about 29. In one embodiment, the median number of cycles administered in a group of patients is about 30. In one embodiment, the median number of cycles administered in a group of patients is greater than about 30 cycles.

In certain embodiments, treatment cycles comprise multiple doses of COMPOUND 1 or COMPOUND 2 administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days).

In one embodiment, depending on the disease to be treated and the subject's condition, the RAS pathway inhibitor, such as a MEK kinase inhibitor, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. In one embodiment, the RAS pathway inhibitor may be formulated, alone or together with COMPOUND 1 and/or one or more active agent(s), in suitable dosage unit with pharmaceutically acceptable excipients, carriers, adjuvants and vehicles, appropriate for each route of administration. In one embodiment, the RAS pathway inhibitor may be formulated, alone or together with COMPOUND 2 and/or one or more active agent(s), in suitable dosage unit with pharmaceutically acceptable excipients, carriers, adjuvants and vehicles, appropriate for each route of administration.

In one embodiment, the RAS pathway inhibitor is administered by, e.g., intravenous (IV), subcutaneous (SC) or oral routes. Certain embodiments herein provide co-administration of the RAS pathway inhibitor with COMPOUND 1 or COMPOUND 2 and/or one or more additional active agents to provide a synergistic therapeutic effect in subjects in need thereof. The co-administered active agent(s) may be cancer therapeutic agents, as described herein. In certain embodiments, the co-administered active agent(s) may be inhibitors of IDH1. In certain embodiments, the co-administered active agent(s) may be inhibitors of IDH2. In certain embodiments, the co-administered agent(s) may be dosed, e.g., orally or by injection (e.g., IV or SC).

In certain embodiments, treatment cycles comprise multiple doses of the RAS pathway inhibitor administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). Suitable dosage amounts for the methods provided herein include, e.g., therapeutically effective amounts and prophylactically effective amounts.

In one embodiment, the RAS pathway inhibitor can be delivered as a single dose such as, e.g., a single bolus injection, or oral tablets or pills; or over time such as, e.g., continuous infusion over time or divided bolus doses over time. In one embodiment, the RAS pathway inhibitor can be administered repetitively if necessary, for example, until the patient experiences stable disease or regression, or until the patient experiences disease progression or unacceptable toxicity. Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In one embodiment, the RAS pathway inhibitor can be administered once daily or divided into multiple daily doses such as twice daily, three times daily, and four times daily. In one embodiment, the administration can be continuous (i.e., daily for consecutive days or every day), intermittent, e.g., in cycles (i.e., including days, weeks, or months of rest when no drug is administered). In one embodiment, the RAS pathway inhibitor is administered daily, for example, once or more than once each day for a period of time. In one embodiment, the RAS pathway inhibitor is administered intermittently, i.e., stopping and starting at either regular or irregular intervals.

Patient Population

In certain embodiments of the methods provided herein, the subject to be treated is an animal, for example a mammal or a non-human primate. In particular embodiments, the subject is a human patient. The subject can be male or female.

Particularly, subjects amenable to treatment according to the methods provided herein include subjects with cancer, wherein the cancer is characterized by the presence of a mutant allele of IDH1 and/or IDH2 and the absence of a mutant allele of NRAS.

In certain embodiments, subjects amenable to treatment according to the methods provided herein include subjects with cancer, wherein the cancer is characterized by the presence of a mutant allele of IDH1 and/or IDH2 and further characterized by a mutant allele of NRAS.

In one embodiment, subjects amenable to treatment according to the methods provided herein include subjects with advanced hematologic malignancies, such as acute myelogenous leukemia (AML), myelodysplastic syndrome (MDS, myeloproliferative neoplasms (MPN), chronic myelomonocytic leukemia (CMML), B-acute lymphoblastic leukemias (B-ALL), or lymphoma (e.g., T-cell lymphoma), each characterized by the presence of a mutant allele of IDH1 and the absence of a mutant allele of NRAS.

In one embodiment, subjects amenable to treatment according to the methods provided herein include subjects with advanced hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and the absence of a mutant allele of NRAS.

In one embodiment, subjects amenable to treatment according to the methods provided herein include subjects with a solid tumor, such as glioma, melanoma, chondrosarcoma, cholangiocarcinoma (e.g., glioma), angioimmunoblastic T-cell lymphoma (AITL), sarcoma, or non small cell lung cancer, each characterized by the presence of a mutant allele of IDH2 and the absence of a mutant allele of NRAS.

In certain embodiments, subjects amenable to treatment according to the methods provided herein include subjects with advanced hematologic malignancies, such as acute myelogenous leukemia (AML), myelodysplastic syndrome (MDS), chronic myelomonocytic leukemia (CMML), myeloid sarcoma, multiple myeloma, lymphoma (e.g., T-cell lymphoma or B-cell lymphoma), angioimmunoblastic T-cell lymphoma (AITL) or blastic plasmacytoid dendritic cell neoplasm, each characterized by the presence of a mutant allele of IDH2 and further characterized by one or more NRAS mutation(s).

In one embodiment, the advanced hematologic malignancy to be treated is AML. In some embodiments, the AML is relapsed and/or refractory. In other embodiments, the AML is untreated. In some embodiments, the AML is relapsed and/or refractory in patients 60 years of age and older. In some embodiments, the AML is untreated in patients 60 years of age and older. In some embodiments, the AML is relapsed and/or refractory in patients under 60 years of age. In one embodiment, COMPOUND 1 is administered as a first line treatment for AML. In one embodiment, COMPOUND 1 is administered as a second line, third line, or fourth line treatment for AML. In one embodiment, COMPOUND 1 is administered after a first line treatment for AML. In one embodiment, COMPOUND 1 is administered after a second line, third line, or fourth line treatment for AML. In one embodiment, COMPOUND 1 is administered after a first relapse. In one embodiment, COMPOUND 1 is administered after primary induction failure. In one embodiment, COMPOUND 1 is administered after re-induction failure. In one embodiment, administration of COMPOUND 1 can occur prior to, during, or after transplant. In one embodiment, COMPOUND 1 is administered after a relapse that is post-transplant. In one embodiment, the AML presentation is subsequent to MPD. In one embodiment, the AML presentation is subsequent to MDS and CMML.

In certain embodiments, subjects amenable to treatment according to the methods provided herein include subjects with a solid tumor, such as glioma, melanoma, chondrosarcoma, cholangiocarcinoma (e.g., glioma), angioimmunoblastic T-cell lymphoma (AITL), sarcoma, or non small cell lung cancer, each characterized by the presence of a mutant allele of IDH2 and further characterized by one or more NRAS mutation(s).

Also encompassed are methods of treating a subject regardless of the subject's age, although some diseases or disorders are more common in certain age groups. In some embodiments, the subject is a human patient at least 18 years old. In some embodiments, the patient is 10, 15, 18, 21, 24, 35, 40, 45, 50, 55, 65, 70, 75, 80, or 85 years old or older.

In certain embodiments, the methods provided herein encompass the treatment of subjects who have not been previously treated for cancer. In other embodiments, the methods encompass treating subjects who have been previously treated but are non-responsive to standard therapies as well as those who are currently being treated for cancer. For example, the subjects may have been previously treated or are currently being treated with a standard treatment regimen for cancer known to the practitioner of skill in the art.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the methods of use provided herein, may be made without departing from the spirit and scope thereof. Patents, patent publications, and other publications referenced herein are incorporated by reference.

EXAMPLES

As used herein, the symbols and conventions used in the examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: CR=complete remission; CRi=complete remision with incomplete blood count recovery; CRp=complete remision with incomplete platelet recovery; MLFS=morphologic leukemia-free state; mNRAS=mutant neuroblastoma RAS Viral Oncogene Homolog; mt=mutant; NRAS=Neuroblastoma RAS Viral Oncogene Homolog; NRASwt=wild-type neuroblastoma RAS viral oncogene homolog; VAF=variant allele frequency; ORR=overall response rate; PD=progressive disease; PR=partial response; SD=stable disease; wt=wild type; g (grams); mg (milligrams); mL (milliliters); mL (microliters); M (molar); mM (millimolar); mM (micromolar); hr or hrs (hour or hours); min (minutes). Unless otherwise specified, the water content in a compound provided herein is determined by Karl Fisher (KF) method.

Example 1. A Phase 1/2, Multicenter, Open-Label, Dose-Escalation and Expansion, Safety, Pharmacokinetic, Pharmacodynamic, and Clinical Activity Study of Orally Administered COMPOUND 1 in Subjects with Advanced Hematologic Malignancies with an IDH2 Mutation Indication: Treatment of patients with advanced hematologic malignancies with an IDH2 mutation.

Phase 1 (Dose Escalation and Part 1 Expansion) Objectives:

Primary Objectives

To assess the safety and tolerability of treatment with COMPOUND 1 administered continuously as a single agent dosed orally on Days 1 to 28 of a 28-day cycle in subjects with advanced hematologic malignancies.

To determine a maximum tolerated dose (MTD) or a maximum administered dose (MAD) and/or the recommended Phase 2 dose (RP2D) of COMPOUND 1 in subjects with advanced hematologic malignancies.

Secondary Objectives

To describe the dose-limiting toxicities (DLTs) of COMPOUND 1 in subjects with advanced hematologic malignancies.

To characterize the pharmacokinetics (PK) of COMPOUND 1 and its metabolite in subjects with advanced hematologic malignancies.

To characterize the PK/pharmacodynamic (PD) relationship of COMPOUND 1 and 2-hydroxygluturate (2-HG).

To characterize the clinical activity associated with COMPOUND 1 in subjects with advanced hematologic malignancies.

Phase 2 Objectives:

Primary Objectives

To assess the efficacy of COMPOUND 1 as treatment for subjects with relapsed or refractory AML with an IDH2 mutation.

Secondary Objectives

To further evaluate the safety profile of COMPOUND 1 in subjects with relapsed or refractory AML with an IDH2 mutation.

To characterize the pharmacokinetics (PK) of COMPOUND 1 and its metabolite in subjects with relapsed or refractory AML with an IDH2 mutation.

To characterize the PK/pharmacodynamic (PD) relationship of COMPOUND 1 and 2-hydroxygluturate (2-HG)

Study Design:

This is a Phase 1/2, multicenter, open-label, 3-part (Phase 1 dose escalation, Phase 1 Part 1 Expansion, and Phase 2), safety, PK/PD, and clinical activity evaluation of orally administered COMPOUND 1 in subjects with advanced hematologic malignancies that harbor an IDH2 mutation. The study includes a dose escalation phase to determine MTD/MAD and/or RP2D, an expansion phase (Part 1) to further evaluate the safety, tolerability, and clinical activity of COMPOUND 1, and a Phase 2 to assess the clinical efficacy of COMPOUND 1 at the RP2D and to further evaluate safety in subjects with refractory and relapsed AML carrying an IDH2 mutation.

Phase 1/Dose Escalation Phase

In the Phase 1 portion, the study includes a dose escalation phase to determine MTD/MAD and/or the RP2D and an expansion phase (Part 1 Expansion) to further evaluate the safety, tolerability and clinical activity of COMPOUND 1 in select populations. The Phase 2 portion (previously Part 2 Expansion) will further inform on the efficacy, safety, tolerability and clinical activity of COMPOUND 1 in subjects with refractory or relapsed AML with an IDH2 mutation.

Dose Escalation Phase: The dose escalation phase will utilize a standard "3+3" design. During the dose escalation phase, consented eligible subjects with relapsed or refractory acute myelogenous leukemia (AML), untreated AML ≥60 years of age who are not candidates for standard therapy, or myelodysplastic syndrome with refractory anemia with excess blasts will be enrolled into sequential cohorts of increasing doses of COMPOUND 1 not to exceed 650 mg QD dose. Each dose cohort will enroll a minimum of 3 subjects. The first 3 subjects enrolled in each dosing cohort during the dose escalation portion of the study will receive a single dose of study drug on Day −3 (i.e., 3 days prior to the start of daily dosing) and undergo safety and PK/PD assessments over 72 hours to evaluate drug concentrations and 2-HG and α-KG levels. The next dose of study drug will be on Cycle 1 Day 1 (C1D1) at which time daily dosing will begin. The initial dosing schedule was twice daily (approximately every 12 hours). Based on the emerging data, a once daily dosing schedule also has been implemented. Alternative dosing schedules (e.g., a loading dose followed by once daily dosing) may continue to be explored in the dose escalation and expansion phases as agreed upon by the Clinical Study Team. If there are multiple subjects in the screening process at the time the third subject within a cohort begins treatment, up to 2 additional subjects may be enrolled with approval of the Medical Monitor. For these additional subjects, the Day −3 through Day 1 PK/PD assessments are optional following discussion with the Medical Monitor.

The safety of dosing during the dose escalation phase will be evaluated by the Clinical Study Team, comprised of the Sponsor designee (Responsible Medical Officer), Study Medical Monitor, and Investigators. The Clinical Study Team will review the emerging safety data from each cohort to determine if dose escalation will occur.

Toxicity severity will be graded according to the National Cancer Institute Common Terminology Criteria for Adverse Events (NCI CTCAE) Version 4.03. A DLT is defined as outlined below.

Non-Hematologic:

All clinically significant non-hematologic toxicities CTCAE ≥Grade 3 with the exception of ≥Grade 3 blood bilirubin increases in subjects with a UDP (uridine diphosphate)-glucuronosyltransferase 1 family, polypeptide A1 (UGT1A1) mutation. In subjects with a UGT1A1 mutation, blood bilirubin increases of >5× upper limit of normal (ULN) may be considered a DLT.

Hematologic:

Prolonged myelosuppression, defined as persistence of ≥Grade 3 neutropenia or thrombocytopenia (by NCI CTCAE, version 4.03, leukemia-specific criteria, i.e., marrow cellularity <5% on Day 28 or later from the start of study drug without evidence of leukemia) at least 42 days after the initiation of Cycle 1 therapy. Leukemia-specific grading should be used for cytopenias (based on percentage decrease from baseline: 50 to 75%=Grade 3, >75%=Grade 4).

Due to frequent co-morbidities and concurrent medications in the population under study, attribution of adverse events (AEs) to a particular drug is challenging. Therefore, all AEs that cannot clearly be determined to be unrelated to COMPOUND 1 will be considered relevant to determining DLTs and will be reviewed by the Clinical Study Team. The Clinical Study Team also will review any other emergent toxicities that are not explicitly defined by the DLT criteria to determine if any warrant a DLT designation.

If, after the third subject completes the 28-day DLT evaluation period (i.e., Cycle 1), no DLTs are observed, the study will proceed with dose escalation to the next cohort following safety review by the Clinical Study Team. If 1 of 3 subjects experiences a DLT during the first cycle, 3 additional subjects will be enrolled in that cohort. If none of the additional 3 subjects experience a DLT, dose escalation may continue to the next cohort following safety review by the Clinical Study Team. If 2 or more subjects in a cohort experience DLTs during the first cycle, dose escalation will be halted and the next lower dose level will be declared the MTD. If the MTD cohort included only 3 subjects, an additional 3 subjects will be enrolled at that dose level to confirm that <2 of 6 subjects experience a DLT at that dose. Alternatively, a dose level intermediate between the non-tolerated dose level and the previously tolerated dose level may be explored and declared the MTD if <2 out of 6 subjects experience a DLT at that dose.

Increases in the dose of COMPOUND 1 for each dose cohort will be guided by an accelerated titration design, where the dose will be doubled (100% increase) from one cohort to the next until COMPOUND 1-related NCI CTCAE Grade 2 or greater toxicity is observed in any subject within the cohort. Following evaluation by the Clinical Study Team, subsequent increases in dose will be 50% or less until the MTD is determined. The absolute percent increase in the dose will be determined by the Clinical Study Team predicated on the type and severity of any toxicity seen in the prior dose cohorts. The MTD is the highest dose that causes DLTs in <2 of 6 subjects.

To optimize the number of subjects treated at a potentially clinically relevant dose, intra-subject dose escalation will be permitted with approval of the Medical Monitor.

Part 1 Expansion Phase

During the Part 1 expansion phase, safety, PK/PD, and preliminary clinical activity data will be reviewed by the Clinical Study Team on an ongoing basis.

In Part 1, 4 non-randomized cohorts of approximately 25 subjects per arm with IDH2-mutated hematologic malignancies will be enrolled as follows:

Arm 1: Relapsed or refractory AML and age ≥60 years, or any subject with AML regardless of age who has relapsed following a bone marrow transplant (BMT).

Arm 2: Relapsed or refractory AML and age <60 years, excluding subjects with AML who have relapsed following a BMT.

Arm 3: Untreated AML and age ≥60 years that decline standard of care chemotherapy.

Arm 4: IDH2-mutated advanced hematologic malignancies not eligible for Arms 1 to 3.

Phase 2

Phase 2, the pivotal part of the study, will further establish the efficacy and safety profile of COMPOUND 1 at the recommended phase 2 dose (RP2D) determined in the ongoing dose escalation phase in subjects with IDH2-mutated relapsed or refractory AML defined as follows:

Subjects who relapse after allogeneic transplantation

Subjects in second or later relapse;

Subjects who are refractory to initial induction or re-induction treatment;

Subjects who relapse within 1 year of initial treatment, excluding patients with favorable-risk status according to NCCN Guidelines. Favorable-risk cytogenetics: inv(16), +(16;16), t(8;21), t(15;17).

Approximately 125 subjects will be enrolled in this part of the trial.

General Study Conduct:

Following informed consent, all subjects will undergo screening procedures within 28 days prior to the C1D1 to determine eligibility. All subjects are required to have confirmation of IDH2-mutated disease from a bone marrow aspirate and peripheral blood. For subjects in the dose escalation phase and Part 1 Expansion, documentation of IDH2 mutation status can be based on local site testing with central laboratory testing performed retrospectively. Subjects in Phase 2 are required to have IDH2-mutation status based on central laboratory testing during screening prior to study treatment. Additional screening procedures include medical, surgical, and medication history, a buccal swab for germ-line mutation analysis, physical examination, vital signs, Eastern Cooperative Oncology Group (ECOG) performance status (PS), 12-lead electrocardiogram (ECG), evaluation of left ventricular ejection fraction (LVEF), clinical laboratory assessments (hematology, chemistry, coagulation, and serum pregnancy test), bone marrow biopsy and aspirate, blood and bone marrow samples for 2-HG and α-KG measurement, and blood for determination of UGT1A1 mutation status. In addition, subjects in the Part 1 Expansion will have urine samples for 2-HG and α-KG measurement and blood samples for cholesterol, and 4β-OH-cholesterol levels collected during screening.

Dose Escalation and Part 1 Expansion

Three days prior to the start of daily dosing of COMPOUND 1 (Day −3), the first 3 subjects enrolled in each cohort in the dose escalation phase and the first 15 subjects enrolled in each arm of Part 1 Expansion will receive a single dose of COMPOUND 1 in clinic and have serial blood and urine samples obtained for determination of blood and urine concentrations of COMPOUND 1, its metabolite (6-(6-(trifluoromethyl)pyridin-2-yl)-N2-(2-(trifluoromethyl)pyridin-4-yl)-1,3,5-triazine-2,4-diamine), 2-HG, and α-KG. A full 72-hour PK/PD profile will be conducted: subjects will be required to remain at the study site for 10 hours on Day −3 and return on Days −2, −1, and 1 for 24-, 48-, and 72-hour samples, respectively. During the in-clinic period on Day −3, clinical observation and serial 12-lead ECGs and vital signs assessments will be conducted. Daily treatment with COMPOUND 1 will begin on C1D1; for subjects in the dose escalation phase and Part 1 Expansion who did not undergo the Day −3 PK/PD assessments, clinical observation and serial 12-lead ECGs and vital signs assessments will be conducted over 8 hours following their first dose of COMPOUND 1 on C1D1.

Subjects in the dose escalation phase and Part 1 Expansion also will undergo PK/PD assessments over a 10-hour period on C1D15, C2D1, and C4D1. Predose blood samples (trough) will be obtained on C1D1 (for those subjects who did not undergo the Day −3 PK/PD assessments), C1D8, C1D22, C2D15, C3D1, C3D15, C5D1, and Day 1 of all cycles thereafter for determination of COMPOUND 1, 2-HG, and α-KG concentrations. These subjects will have urine collected for PK/PD evaluation at screening; prior to dosing on C1D15, C2D1 and Day 1 of all cycles thereafter; and at the End of Treatment visit. Available bone marrow biopsy samples also will be assessed for 2-HG and α-KG levels.

Phase 2

Subjects in the Phase 2 portion of the trial are not required to undergo the Day −3 assessments; these subjects will undergo an 8-hour PK/PD profile conducted on Day 1 of Cycles 1 and 2, and predose blood samples (trough) on C1D2 and C2D2 will be obtained in order to assess PK/PD in a 24-hour period. Additional blood samples for PK/PD assessments will be drawn pre-dose (within 30 minutes) on Day 1 of Cycle 3, and at the End of Treatment visit. Time-matched 12-lead ECGs will be conducted in triplicate on Day 1 of Cycles 1 and 2; a triplicate ECG is also to be obtained at the End of Treatment visit. Single 12-lead ECGs will be conducted on Day 1 of every cycle beginning with Cycle 3, and at the Follow-up visit. Available bone marrow biopsy samples will be assessed for 2-HG and α-KG levels.

Other Safety Assessments (All Phases)

All subjects will undergo safety assessments during the treatment period to include physical examination, vital signs, ECOG PS, 12-lead ECGs, evaluation of LVEF, and clinical laboratory assessments (hematology, chemistry, coagulation, and pregnancy testing).

Clinical Activity Assessments:

Phase 1 (Dose Escalation and Part 1 Expansion)

Subjects in the dose escalation phase and Part 1 Expansion will have the extent of their disease assessed, including bone marrow biopsies and/or aspirates and peripheral blood, at screening, on C1D15, C2D1, and C3D1, every 28 days (peripheral blood only) or every 56 days (bone marrow biopsies and/or aspirates and peripheral blood) thereafter while on study drug treatment, independent of dose delays and/or dose interruptions, and/or at any time when progression of disease is suspected. Response to treatment and treatment decisions in all subjects will be determined by the Investigators based on modified International Working Group (IWG) response criteria or other appropriate response criteria for the malignancy under study.

Phase 2

For subjects enrolled in the Phase 2 portion of the trial, extent of disease, including bone marrow biopsies and/or aspirates and peripheral blood, will be assessed at screening, on C2D1, every 28 days thereafter through 12 months, and every 56 days thereafter while on study drug treatment, independent of dose delays and/or dose interruptions, and/or at any time when progression of disease is suspected. Eligibility, treatment decisions, and response to treatment will be determined by the Investigators based on modified International Working Group (IWG) response criteria. Response will be also be assessed retrospectively by an Independent Response Adjudication Committee (IRAC).

End of Treatment and Follow-Up:

Subjects may continue treatment with COMPOUND 1 until disease progression or development of unacceptable toxicity.

Evidence supports that cancer-associated IDH mutations block normal cellular differentiation and promote tumorigenesis via the abnormal production of 2-HG, a potential oncometabolite. COMPOUND 1 may produce antitumor effects by reversing the differentiation block induced by the IDH2 mutations and promoting appropriate cellular differentiation.

Because of the unique mechanism of action of COMPOUND 1, clinical responses are different than those observed with cytotoxic agents. Responses with COMPOUND 1 may be occur after 2 or more cycles of therapy and they may occur after an initiation period of leukocytosis in the peripheral blood and/or bone marrow with, in rare cases, corresponding clinical signs and symptoms of fever, fluid retention, hypoxia, and skin rash which have been termed a differentiation-like syndrome.

As such, standard assessment criteria developed based on the experience from the cytotoxic chemotherapeutic agents do not provide a complete and accurate response assessment for this novel class of IDH2 inhibitors. Therefore, in the setting where a subject's assessment shows signs similar to progression within the first 2 cycles, caution should be exercised in discontinuing study drug, and a discussion with the Medical Monitor is required, especially in situations where the subject's clinical condition is stable as supported by, but limited to, absence of signs and symptoms of rapid deterioration indicating disease progression and/or general condition is stable or improving.

Subjects who experience progression of disease (PD) per the applicable response criteria, should have assessment of the disease repeated 28 days later in order to confirm PD with option of continuing treatment as described above while awaiting for confirmation. If repeat evaluation confirms PD subjects will discontinue study treatment and proceed to the survival follow-up phase.

Subjects with stable or progressive disease may continue to receive study treatment with COMPOUND 1 at the discretion of the Investigator and with Medical Monitor approval.

All subjects are to undergo an end of treatment assessment (within approximately 5 days of the last dose of study drug); in addition, a follow-up safety assessment is to be scheduled 28 days after the last dose. Furthermore, all subjects will be followed monthly for disease status, overall survival, and initiation of non-study anti-neoplastic therapy, until death, withdrawal of consent, or the end of the study, whichever occurs first.

Subjects who achieve an adequate response to treatment with COMPOUND 1 and meet other criteria required to undergo hematopoietic stem cell transplant (HSCT) may proceed to HSCT after discontinuation of study therapy. Those subjects will be followed on study for outcome until relapse or end of study to support the overall clinical benefit of COMPOUND 1 in this setting.

Subjects who relapse following HSCT may be eligible to restart treatment with COMPOUND 1 with Medical Monitor approval and at the discretion of the Investigator, if they have confirmed recurrent IDH2 mutant positive disease, no other cancer treatment (with the exception of anti-neoplastic therapies used in the course of HSCT such as conditioning regimen or induction-type regimen and anti-GVHD prophylaxis [i.e., methotrexate]) besides HSCT was administered since the last dose of COMPOUND 1, the subject meets the safety parameters listed in the Inclusion/Exclusion criteria, and the trial is open. Subjects will resume COMPOUND 1 therapy at the same dose and schedule at the time of COMPOUND 1 treatment discontinuation prior to HSCT.

All subjects, including those who relapse following HSCT and elect not to restart treatment, will be followed monthly thereafter for assessment of survival status and non-study anti-neoplastic therapies since discontinuation of study drug until death or end of study.

Number of Subjects (Planned):

Approximately a minimum of 291 subjects in total is planned to be enrolled in the study (i.e., in the dose escalation, Part 1 Expansion, and Phase 2 portion of the trial).

Assuming that identification of the MTD/MAD requires the evaluation of 13 dose levels/schedules of COMPOUND 1 with up to 5 subjects per dose level, with the exception that the MTD/MAD requires 6 subjects, then 66 subjects will be enrolled during the dose escalation part of the study. Additional subjects may be needed for cohort expansion during dose escalation, for the replacement of subjects who are not evaluable for PK/PD, safety, or clinical activity, or for evaluation of alternative dosing regimens other than the planned escalation scheme or the MTD/MAD, to optimize the RP2D and regimen(s). As of April 2015, 5 dose levels (ranging from 30 mg to 150 mg) have been evaluated in the BID schedule and 8 dose levels (ranging from 50 mg to 650 mg) have been evaluated in the QD schedule.

Four cohorts of a minimum of 25 additional subjects in specific hematologic malignancy subsets (total a minimum of 100 subjects) will be enrolled in Part 1 Expansion of the study.

The Phase 2 portion of the trial will enroll approximately 125 subjects with relapsed or refractory AML with an IDH2 mutation. Additional subjects may be needed for the replacement of subjects who are not evaluable for PK/PD, safety, and/or clinical activity, or for evaluation of alternative dosing regimens. The final total sample size may be adjusted according to the observed toxicity rate, and number of subjects enrolled for expanded evaluation.

Inclusion Criteria

Subjects must meet all of the following criteria to be enrolled in the study:

1. Subject must be ≥18 years of age.
2. Subjects must have advanced hematologic malignancy including:

Phase 1/Dose Escalation:
Diagnosis of AML according to World Health Organization (WHO) criteria;
Disease refractory or relapsed (defined as the reappearance of >5% blasts in the bone marrow).
Untreated AML, ≥60 years of age and are not candidates for standard therapy due to age, performance status, and/or adverse risk factors, according to the treating physician and with approval of the Medical Monitor;
Diagnosis of MDS according to WHO classification with refractory anemia with excess blasts (subtype RAEB-1 or RAEB-2), or considered high-risk by the Revised International Prognostic Scoring System (IPSS-R) that is recurrent or refractory, or the subject is intolerant to established therapy known to provide clinical benefit for their condition (i.e., subjects must not be candidates for regimens known to provide clinical benefit), according to the treating physician and with approval of the Medical Monitor. (Subjects with other relapsed and/or primary refractory hematologic cancers, for example CMML, who fulfill the inclusion/excluding criteria may be considered on a case-by case basis, with approval of the Medical Monitor.)

Phase 1/Part 1 Expansion:
Arm 1: Relapsed or refractory AML and age ≥60 years, or any subject with AML regardless of age who has relapsed following a BMT.
Arm 2: Relapsed or refractory AML and age <60 years, excluding subjects with AML who have relapsed following a BMT.
Arm 3: Untreated AML and age ≥60 years that decline standard of care chemotherapy.
Arm 4: IDH2-mutated advanced hematologic malignancies not eligible for Arms 1 to 3.

Phase 2:
Diagnosis of AML according to World Health Organization (WHO) criteria and disease relapsed or refractory as defined by:
Subjects who relapse after allogeneic transplantation;
Subjects in second or later relapse;
Subjects who are refractory to initial induction or re-induction treatment;
Subjects who relapse within 1 year of initial treatment, excluding patients with favorable-risk status according to NCCN Guidelines. Favorable-risk cytogenetics: inv(16), +(16;16), t(8;21), t(15;17).

3. Subjects must have documented IDH2 gene-mutated disease:
For subjects in the dose escalation phase and Part 1 Expansion, IDH2 mutation may be based on local evaluation. (Centralized testing will be performed retrospectively).

4. For subjects in the Phase 2 portion of the trial, central testing of IDH2 mutation in samples of bone marrow aspirate and peripheral blood, is required during screening to confirm eligibility. Subjects must be amenable to serial bone marrow sampling, peripheral blood sampling, and urine sampling during the study.
The diagnosis and evaluation of AML or MDS will be made by bone marrow aspiration and biopsy. If an aspirate is unobtainable (i.e., a "dry tap"), the diagnosis may be made from the core biopsy.
Screening bone marrow aspirate and peripheral blood samples are required for all subjects. A bone marrow biopsy must be collected if adequate aspirate is not attainable unless:
A bone marrow aspirate and biopsy was performed as part of the standard of care within 28 days prior to the start of the study treatment; and Slides of bone marrow aspirate, biopsy and stained peripheral blood smear are available for both local and central pathology reviewers;
5. Subjects must be able to understand and willing to sign an informed consent. A legally authorized representative may consent on behalf of a subject who is otherwise unable to provide informed consent, if acceptable to, and approved by, the site and/or site's Institutional Review Board (IRB)/Independent Ethic Committee (IEC).
6. Subjects must have ECOG PS of 0 to 2.
7. Platelet count ≥20,000/μL (Transfusions to achieve this level are allowed.) Subjects with a baseline platelet count of <20,000/μL due to underlying malignancy are eligible with Medical Monitor approval.
8. Subjects must have adequate hepatic function as evidenced by:
   Serum total bilirubin −1.5× upper limit of normal (ULN), unless considered due to Gilbert's disease, a gene mutation in UGT1A1, or leukemic organ involvement, following approval by the Medical Monitor;
   Aspartate aminotransferase (AST), alanine aminotransferase (ALT), and alkaline phosphatase (ALP)≤3.0× ULN, unless considered due to leukemic organ involvement.
9. Subjects must have adequate renal function as evidenced by:
   Serum creatinine ≤2.0×ULN
   OR
   Creatinine clearance >40 mL/min based on the Cockroft-Gault glomerular filtration rate (GFR) estimation:

(140−Age)×(weight in kg)×(0.85 if female)/72×serum creatinine

10. Subjects must be recovered from any clinically relevant toxic effects of any prior surgery, radiotherapy, or other therapy intended for the treatment of cancer. (Subjects with residual Grade 1 toxicity, for example Grade 1 peripheral neuropathy or residual alopecia, are allowed with approval of the Medical Monitor.)
11. Female subjects with reproductive potential must agree to undergo medically supervised pregnancy test prior to starting study drug. The first pregnancy test will be performed at screening (within 7 days prior to first study drug administration), and on the day of the first study drug administration and confirmed negative prior to dosing and Day 1 before dosing all subsequent cycles.
12. Female subjects with reproductive potential must have a negative serum pregnancy test within 7 days prior to the start of therapy. Subjects with reproductive potential are defined as sexually mature women who have not undergone a hysterectomy, bilateral oophorectomy or tubal occlusion or who have not been naturally postmenopausal (i.e., who have not menstruated at all) for at least 24 consecutive months (i.e., has had menses at any time in the preceding 24 consecutive months). Females of reproductive potential as well as fertile men and their partners who are female of reproductive potential must agree to abstain from sexual intercourse or to use two highly effective forms of contraception from the time of giving informed consent, during the study and for 120 days (females and males) following the last dose of COMPOUND 1. A highly effective form of contraception is defined as hormonal oral contraceptives, injectables, patches, intrauterine devices, double-barrier method (e.g., synthetic condoms, diaphragm, or cervical cap with spermicidal foam, cream, or gel), or male partner sterilization.
13. Able to adhere to the study visit schedule (ie, clinic visits at the study sites are mandatory, unless noted otherwise for particular study visits) and other protocol requirements Exclusion Criteria Subjects who meet any of the following criteria will not be enrolled in the study:
1. Subjects who have undergone a hematopoietic stem cell transplant (HSCT) within 60 days of the first dose of COMPOUND 1, or subjects on immunosuppressive therapy post HSCT at the time of screening, or with clinically significant graft-versus-host disease (GVHD). (The use of a stable dose of oral steroids post HSCT and/or topical steroids for ongoing skin GVHD is permitted with Medical Monitor approval.)
2. Subjects who received systemic anticancer therapy or radiotherapy <14 days prior to their first day of study drug administration. (Hydroxyurea is allowed prior to enrollment and after the start of COMPOUND 1 for the control of peripheral leukemic blasts in subjects with leukocytosis (white blood cell [WBC] counts >30,000/μL).
3. Subjects who received a small molecule investigational agent <14 days prior to their first day of study drug administration. In addition, the first dose of COMPOUND 1 should not occur before a period ≥5 half-lives of the investigational agent has elapsed.
4. Subjects taking the following sensitive CYP substrate medications that have a narrow therapeutic range are excluded from the study unless they can be transferred to other medications within ≥5 half-lives prior to dosing: paclitaxel (CYP2C8) warfarin, phenytoin (CYP2C9), S-mephenytoin (CYP2C19), thioridazine (CYP2D6), theophylline and tizanidine (CYP1A2).
5. Subjects taking the P-gp and BCRP transporter-sensitive substrates digoxin and rosuvastatin should be excluded from the study unless they can be transferred to other medications within ≥5 half-lives prior to dosing.
6. Subjects for whom potentially curative anticancer therapy is available.
7. Subjects who are pregnant or lactating.
8. Subjects with an active severe infection that required anti-infective therapy or with an unexplained fever >38.5° C. during screening visits or on their first day of study drug administration (at the discretion of the Investigator, subjects with tumor fever may be enrolled).
9. Subjects with known hypersensitivity to any of the components of COMPOUND 1.
10. Subjects with New York Heart Association (NYHA) Class III or IV congestive heart failure or LVEF <40% by echocardiogram (ECHO) or multi-gated acquisition (MUGA) scan obtained within approximately 28 days of C1D1.
11. Subjects with a history of myocardial infarction within the last 6 months of screening.
12. Subjects with uncontrolled hypertension (systolic blood pressure [BP]>180 mmHg or diastolic BP >100 mmHg) at screening are excluded. Subjects requiring 2 or more medications to control hypertension are eligible with Medical Monitor approval.

13. Subjects with known unstable or uncontrolled angina pectoris.
14. Subjects with a known history of severe and/or uncontrolled ventricular arrhythmias.
15. Subjects with a QTcF (QT corrected based on Fridericia's equation) interval >450 msec or other factors that increase the risk of QT prolongation or arrhythmic events (e.g., heart failure, hypokalemia, family history of long QT interval syndrome) at screening. Subjects with bundle branch block and a prolonged QTc interval should be reviewed by the Medical Monitor for potential inclusion.
16. Subjects taking medications that are known to prolong the QT interval unless they can be transferred to other medications within ≥5 half-lives prior to dosing.
17. Subjects with known infection with human immunodeficiency virus (HIV) or active hepatitis B or C.
18. Subjects with any other medical or psychological condition, deemed by the Investigator to be likely to interfere with a subject's ability to sign informed consent, cooperate, or participate in the study.
19. Subjects with known dysphagia, short-gut syndrome, gastroparesis, or other conditions that limit the ingestion or gastrointestinal absorption of drugs administered orally.
20. Subjects with clinical symptoms suggesting active central nervous system (CNS) leukemia or known CNS leukemia. Evaluation of cerebrospinal fluid is only required if there is a clinical suspicion of CNS involvement by leukemia during screening.
21. Subjects with immediately life-threatening, severe complications of leukemia such as uncontrolled bleeding, pneumonia with hypoxia or shock, and/or disseminated intravascular coagulation.
22. In the Phase 2 portion of the trial only, subjects who have previously received treatment with an inhibitor of IDH.

Investigational Product, Dosage and Mode of Administration:

COMPOUND 1 (mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol) will be provided as 5, 10, 25, 50, 100, 150 and 200 mg free-base equivalent strength tablets to be administered orally.

Phase 1/Dose Escalation

The first 3 subjects in each cohort in the dose escalation portion of the study and the first 15 subjects in each arm of Part 1 Expansion will receive a single dose of study drug on Day −3; their next dose of study drug will be administered on C1D1 at which time subjects will start daily dosing on Days 1 to 28 in 28-day cycles. Starting with C1D1, dosing is continuous; there are no inter-cycle rest periods. Subjects who are not required to undergo the Day −3 PK/PD assessments will initiate daily dosing with COMPOUND 1 on C1D1.

Subjects are required to fast (water is allowed) for 2 hours prior to study drug administration and for 1 hour following study drug administration.

The dose of COMPOUND 1 administered to a subject will be dependent upon which dose cohort is open for enrollment when the subject qualifies for the study. The starting dose of COMPOUND 1 to be administered to the first cohort of subjects is 30 mg administered orally twice a day, and the maximum administered dose of COMPOUND 1 to be administered is 650 mg administered orally once a day.

Phase 1/Part 1 Expansion and Phase 2

The starting dose of COMPOUND 1 recommended for evaluation is 100 mg QD. This is based on the safety, PK, pharmacodynamics and clinical activity of COMPOUND 1 observed to date in AG221-C-001. Evaluation of pharmacodynamic response demonstrated sustained reduction in 2-HG plasma levels by Day 1 of Cycle 2 and up to 98% inhibition in most subjects with R140Q mutation at all doses. Increasing dose is associated with higher exposure and inhibition of 2-HG in subjects with R172K mutation. Importantly, preliminary efficacy data of the 44 subjects treated at 100 mg QD has shown an overall response rate of 36.4%. Thus a dose of 100 mg should adequately achieve inhibition of 2-HG in subjects with either R140Q or R172K mutation. Moreover, the safety profile at 100 mg, including ≥Grade 3, is consistent with that of lower doses.

Intra-subject dose escalation is possible.

A subset of the clinical samples from the trial described in Example 1 were analyzed at screening. Sample types included bone marrow, peripheral blood and mononuclear cells isolated from bone marrow or peripheral blood. DNAs were extracted from these samples and sequenced at Foundation Medicine (Heme Panel, see http://foundationone.com/learn.php) using next generation sequencing technique.

Duration of Treatment:

Subjects may continue treatment with COMPOUND 1 until disease progression or development of unacceptable toxicity. Subjects who experience disease progression per the applicable response criteria who are, in the opinion of the Investigator, benefiting from treatment may be allowed to continue on study drug with approval of the Medical Monitor.

End of Study:

End of study is defined as the time at which:
  all subjects have discontinued treatment with COMPOUND 1 and have been followed for survival for at least 12 months, or have died, been lost to follow up, or withdrew consent prior to at least 12 months of follow-up
  or the date of receipt of the last data point from the last subject that is required for primary, secondary and/or exploratory analysis, as pre-specified in the protocol and/or the Statistical Analysis Plan (SAP), whichever is the later date.

Criteria for Evaluation:

Safety:

Monitoring of AEs, including determination of DLTs, serious adverse events (SAEs), and AEs leading to discontinuation; safety laboratory parameters; physical examination findings; vital signs; 12-lead ECGs; LVEF; and ECOG PS.

The severity of AEs will be assessed by the NCI CTCAE, Version 4.03.

Pharmacokinetics and Pharmacodynamics:

Serial blood sampling for determination of concentration-time profiles of COMPOUND 1 and its metabolite (6-(6-(trifluoromethyl)pyridin-2-yl)-N2-(2-(trifluoromethyl)pyridin-4-yl)-1,3,5-triazine-2,4-diamine). Urine sampling for determination of concentrations of COMPOUND 1 and its metabolite (6-(6-(trifluoromethyl)pyridin-2-yl)-N2-(2-(trifluoromethyl)pyridin-4-yl)-1,3,5-triazine-2,4-diamine) (dose escalation and Part 1 expansion subjects only). Blood and bone marrow sampling for determination of 2-HG and α-KG levels.

Clinical Activity:

Serial blood and bone marrow sampling to determine response to treatment based on modified IWG response criteria or other appropriate response criteria based on the malignancy under study.

Overall response rate (ORR), the primary efficacy endpoint, is defined as the rate of responders including complete remission (CR), CR with incomplete platelet recovery (CRp), marrow CR (mCR) (morphologic leukemia-free state [MLFS] for subjects with AML), CR with incomplete hematologic recovery (CRi), and partial remission (PR). Other measures of clinical activity including complete remission rate (CRR), duration of remission/response, event-free survival, overall survival, and time to remission/response will be summarized.

For Phase 1 Dose Escalation/Part 1 Expansion, the efficacy analysis of response rates as assessed by the site Investigators using modified International Working Group (IWG) response criteria will be conducted in Full Analysis Set for each dose level, expansion arm, and overall if appropriate. The analysis of Part 1 expansion arms may also include subjects from the dose-escalation phase who received the same dose/regimen as subjects in the expansion arms and who meet the eligibility criteria of individual arms.

For Phase 2 portion of the trial, the primary efficacy analysis of COMPOUND 1 will be determined by the Investigators based on modified International Working Group (IWG) response criteria. Response will be also be assessed retrospectively by an Independent Response Adjudication Committee (IRAC) using the Full Analysis Set (FAS). Key supportive analyses will be based on independent central review of response in FAS.

In certain embodiments, the patients with AML characterized by somatic mutations in NRAS are resistant to treatment of COMPOUND 1.

In certain embodiments, a combination therapy with COMPOUND 1 and one or more compounds that target RAS pathways (e.g. MEK compounds including Trametinib, Selumetinib, Binimetinib, PD-325901, Cobimetinib, CI-1040 or PD035901) is effective in treating AML in patients with AML characterized by somatic mutations in NRAS.

Example 2: NRAS Mutation Status and COMPOUND 1 Response

A subset of the clinical samples from the trial described in Example 1 were analyzed at screening. Sample types included bone marrow, peripheral blood and mononuclear cells isolated from bone marrow or peripheral blood. DNAs were extracted from these samples and sequenced at Foundation Medicine (see http://foundationone.com/learn.php) using next generation sequencing technique.

The characteristics of the analyzed sample set is provided in Table 7:

TABLE 7

|  | Analyzed Population (N = 118) |
|---|---|
| Age (years), median (min-max) | 66.3 (29-90) |
| Gender, % M/F | 58/42 |
| IDH2 mutation, n (%) | |
| R140 | 91 (77) |
| R172 | 23 (19) |

TABLE 7-continued

|  | Analyzed Population (N = 118) |
|---|---|
| Diagnosis, n (%) | |
| RR-AML | 88 (75) |
| Untreated AML | 12 (10.1) |
| MDS | 10 (8.5) |
| Other | 8 (6.8) |

The characteristics of the clinical population in the trial described in Example 1 is provided in Table 8:

TABLE 8

|  | All patients (N = 209) |
|---|---|
| Age (years), median (min-max) | 69 (19-100) |
| Gender, % M/F | 56/44 |
| IDH2 mutation, n (%) | |
| R140 | 146 (70) |
| R172 | 50 (24) |
| Diagnosis, n (%) | |
| RR-AML | 159 (76) |
| Untreated AML | 24 (11) |
| MDS | 14 (7) |
| Other | 12 (6) |

Analysis

A total of 60 genes were identified to carry at least one mutation in the analyzed set (including IDH2 gene). Fisher's exact test was conducted to evaluate the association of somatic mutations with clinical response (responders include CR, CRp, CRi and PR, indicated as +, while none-responders include SD and PD, indicated as − in Table 9). The P-values were adjusted by multiple-test correction.

Results

Figure 7:
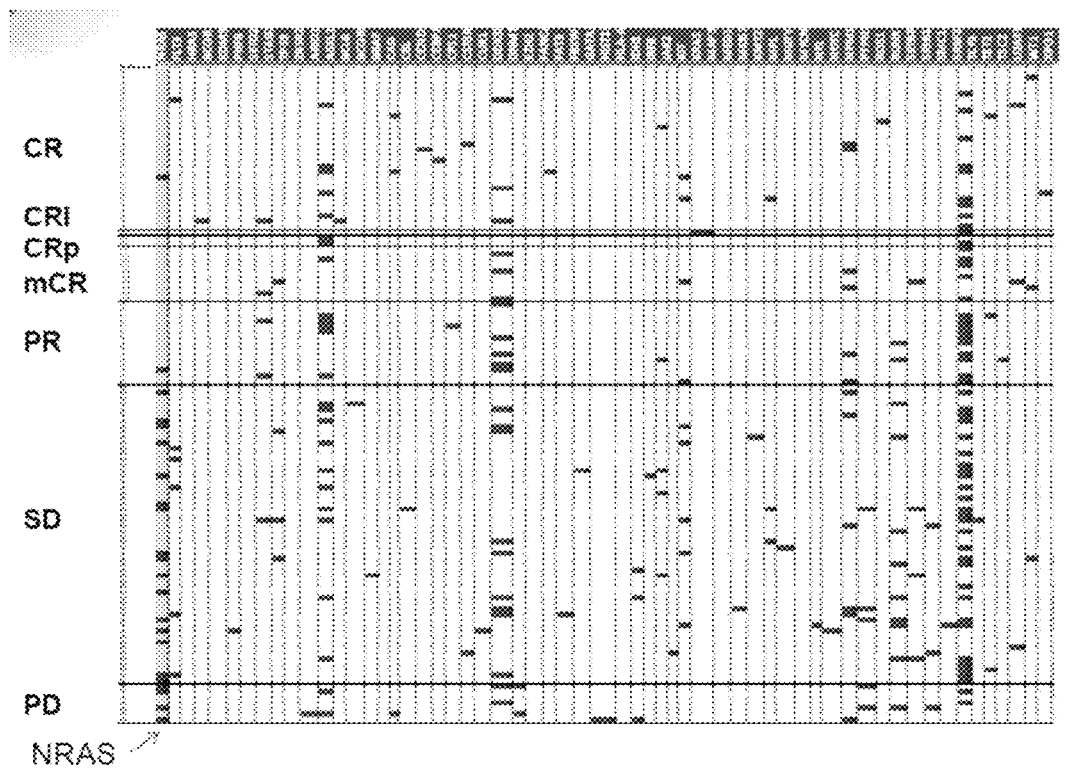
FIG. 7 illustrates the comutations, including NRAS mutations, in samples treated with for COMPOUND 1 according to response categories.

NRAS was the only gene whose mutation status was significantly associated with COMPOUND 1 response. FIG. 7 provides a visual of comutations, including NRAS mutations according to response categories. FIG. 7 profiles bone marrow at screening visit for patients only where genes were mutated in ≥2. In FIG. 7, genes (y-axis) are shown in decreasing order of frequency, with the exception of IDH1, while patients (x-axis) are grouped by response then by similarity in alterations; only patients from dose escalation phase with an evaluable response included.

Table 9 below provides results of the analysis:

TABLE 9

|  |  | NRAS mutation | |
|---|---|---|---|
|  |  | + | − |
| Response status | + | 2 | 55 |
|  | − | 21 | 40 | p-value - 1.417e−05
Adjusted p = 0.0014

Mutation status positive (+) means any known mutation(s) in NRAS, and negative (−) means no mutation in NRAS was present.

Positive response status (+) includes CR, mCR and PR and negative response status (−) includes stable disease (SD) and pregressive disease (PD).

As seen from the data in Table 9, known somatic mutations in NRAS are present more frequently in COMPOUND 1 none-responders, represented by stable disease (SD) and progressive patients.

Example 3: A Phase 1, Multicenter, Open-Label, Dose-Escalation, Safety, Pharmacokinetic, Pharmacodynamic, and Clinical Activity Study of Orally Administered COMPOUND 2 in Subjects with Advanced Hematologic Malignancies with an IDH1 Mutation Indication:

Treatment of patients with advanced hematologic malignancies with an IDH1 mutation.

Objectives:

Primary:

To assess the safety and tolerability of treatment with COMPOUND 2 administered continuously as a single agent dosed orally on Days 1 to 28 of a 28-day cycle in subjects with advanced hematologic malignancies. The initial dosing regimen will be twice daily (approximately every 12 hours). If warranted based on the emerging data, an alternative dosing schedule (e.g., once daily or three times daily), including administration of the same total daily dose using different dosing schedules in concurrent cohorts, may be explored as agreed upon by the Clinical Study Team.

To determine the maximum tolerated dose (MTD) and/or the recommended Phase 2 dose of COMPOUND 2 in subjects with advanced hematologic malignancies.

To assess the clinical activity of AG-120 in subjects with relapsed or refractory acute myelogenous leukemia (AML) with an IDH1 mutation who are enrolled in Arm 1 of the expansion phase.

Secondary:

To describe the dose-limiting toxicities (DLTs) of COMPOUND 2 in subjects with advanced hematologic malignancies.

To characterize the pharmacokinetics (PK) of COMPOUND 2 in subjects with advanced hematologic malignancies.

To evaluate the PK/pharmacodynamic (PD) relationship of COMPOUND 2 and 2-hydroxygluturate (2 HG).

To characterize the clinical activity associated with COMPOUND 2 in subjects with advanced hematologic malignancies.

Methodology:

This study is a Phase 1, multicenter, open-label, dose-escalation, safety, PK/PD, and clinical activity evaluation of orally administered COMPOUND 2 in subjects with advanced hematologic malignancies that harbor an IDH1 mutation. The study includes a dose escalation phase to determine MTD and/or RP2D followed by expansion arms to further evaluate the safety, tolerability, and clinical activity of COMPOUND 2 in select populations.

Dose Escalation Phase

The dose escalation phase will utilize a standard "3+3" design. During the dose escalation phase, consented eligible subjects with relapsed or refractory AML, untreated AML ≥60 years of age who are not candidates for standard therapy, or myelodysplastic syndrome (MDS) with refractory anemia with excess blasts will be enrolled into sequential cohorts of increasing doses of COMPOUND 2. Each dose cohort will plan to enroll a minimum of 3 subjects. The first 3 subjects enrolled in each dosing cohort during the dose escalation phase of the study will initially receive a single dose of study drug on Day 3 (i.e., 3 days prior to the start of daily dosing) and undergo PK/PD assessments over 72 hours to evaluate drug concentrations and 2-HG levels. The next dose of study drug will be on Cycle 1 Day 1 (C1D1) at which time daily dosing will begin. The initial dosing regimen was twice daily (approximately every 12 hours). Based on the emerging data, a once daily (approximately every 24 hours) dosing schedule has been implemented. Alternative dosing schedules, including administration of the same total daily dose using different dosing schedules in concurrent cohorts, may be explored as agreed upon by the Clinical Study Team. If there are multiple subjects in the screening process at the time the third subject within a cohort begins treatment, up to 2 additional subjects may be enrolled with approval of the Medical Monitor. For these additional subjects, the Day 3 through Day 1 PK/PD assessments may be considered optional following discussion with the Medical Monitor.

The safety of dosing during the dose escalation phase will be evaluated by the Clinical Study Team, comprised of the Sponsor (Responsible Medical Officer), Study Medical Monitor, and Investigators. The Clinical Study Team will review the emerging safety data from each cohort to determine if dose escalation will occur.

Toxicity severity will be graded according to the National Cancer Institute Common Terminology Criteria for Adverse Events (NCI CTCAE) version 4.03. A DLT is defined as outlined below.

Non-hematologic:

All non-hematologic toxicities CTCAE ≥Grade 3.

Hematologic:

Prolonged myelosuppression with persistence of ≥Grade 4 neutropenia or thrombocytopenia in the absence of leukemia (blast count <5%) at least 42 days after the initiation of Cycle 1 therapy.

Due to frequent co-morbidities and concurrent medications in the population under study, attribution of adverse events (AEs) to a particular drug is challenging. Therefore, all AEs that cannot clearly be determined to be unrelated to COMPOUND 2 will be considered relevant to determining DLTs and will be reviewed by the Clinical Study Team. The Clinical Study Team also will review any other emergent toxicities that are not explicitly defined by the DLT criteria to determine if any warrant a DLT designation.

If, after the third subject completes the 28-day DLT evaluation period (i.e., Cycle 1), no DLTs are observed, the study will proceed with dose escalation to the next cohort following safety review by the Clinical Study Team. If 1 of 3 subjects experiences a DLT during the first cycle, 3 additional subjects will be enrolled in that cohort. If none of the additional 3 subjects experience a DLT, dose escalation may continue to the next cohort following safety review by the Clinical Study Team. If 2 or more subjects in a cohort experience DLTs during the first cycle, dose escalation will be halted and the next lower dose level will be declared the MTD. Alternatively, a dose level intermediate between the dose level exceeding MTD and the previous does level may be explored and declared MTD if <2 out of 6 subjects experience a DLT at that dose. If the MTD cohort included only 3 subjects, an additional 3 subjects will be enrolled at that dose level to confirm that <2 of 6 subjects experience a DLT at that dose.

Increases in the dose of AG-120 for each dose cohort will be guided by an accelerated titration design, where the daily dose may be doubled (100% increase) from one cohort to the next until AG-120-related CTCAE Grade 2 or greater toxicity is observed in any subject within the cohort. Following evaluation by the Clinical Study Team, subsequent increases in dose will be guided by the observed toxicity, and potentially PK and PK/PD data, until the MTD is determined. The absolute percent increase in the daily dose will be determined by the Clinical Study Team predicated on the type and severity of any toxicity seen in the prior dose cohorts (but will never exceed 100%). The MTD is the highest dose that causes DLTs in <2 of 6 subjects.

If no DLTs are identified during the dose escalation phase, dose escalation may continue for at least 2 dose levels above the projected maximum clinically effective exposure, as determined by an ongoing assessment of PK/PD and any observed clinical activity; this may occur in parallel with the expansion phase.

To optimize the number of subjects treated at a potentially clinically relevant dose, intra-subject dose escalation will be permitted with approval of the Medical Monitor.

Expansion Phase

Following determination of the recommended dose and dosing regimen from the dose escalation phase, the expansion phase will open to further explore the dose in subjects with specific hematologic malignancies. During the expansion phase, 4 non-randomized arms of approximately 25 subjects per arm with IDH1-mutated hematologic malignancies will be enrolled as follows:

Arm 1: Relapsed or refractory AML defined as:
Subjects who relapse after transplantation;
Subjects in second or later relapse;
Subjects who are refractory to initial induction or reinduction treatment.
Subjects who relapse within 1 year of initial treatment, excluding patients with favorable-risk status according to NCCN Guidelines, version 1.2015.

Arm 2: Untreated AML who are not candidates for standard therapy due to age, comorbid condition, performance status, and/or adverse risk factors, according to the Investigator and with approval of the Medical Monitor.

Arm 3: Other non-AML IDH1-mutated relapsed and/or refractory advanced hematologic malignancies, where no standard of care treatment option is available. Such as:
Myelodysplastic syndrome that is recurrent or refractory after having failed hypomethylating agent(s) and with the approval of Medical Monitor.
Relapsed and/or primary refractory chronic myelomonocytic leukemia [CMML] with the approval of Medical Monitor.
Other non-AML IDH1-mutated relapsed and/or refractory advanced hematologic malignancy, that have failed standard of care or no standard of care treatment option is available according to the Investigator and with the approval of the Medical Monitor.

Arm 4: Relapsed AML patients not eligible for Arm 1 that have failed available standard of care or are unable to receive standard of care due to age, comorbid condition, performance status, and/or adverse risk factors, according to the Investigator and with approval of the Medical Monitor.

An interim analysis for safety and futility will be conducted for Arm 1 of the expansion phase at the time at which the first 25 subjects have been treated and followed for 2 cycles or discontinued earlier. If the objective response rate (ORR), defined as including all responses of complete remission (CR), CR with incomplete platelet recovery (CRp), morphologic leukemia-free state (MLFS), CR with incomplete hematologic recovery (CRi), and partial remission (PR), is <15% (i.e., <4 responders), then additional enrollment into Arm 1 may be terminated; if the ORR is ≥15%, an additional approximately 100 subjects will be enrolled. Enrollment will not be held for the interim analysis.

General Study Conduct

Following informed consent, all subjects will undergo screening procedures within 28 days prior to C1D1 to determine eligibility. All subjects are required to have confirmation of IDH1 R132 gene-mutated disease from a bone marrow aspirate and/or biopsy. For subjects in the dose escalation phase, documentation can be based on local site testing with central laboratory testing performed retrospectively. Subjects in the expansion phase are required to have IDH1 R132 gene-mutated disease based on central laboratory testing during screening prior to treatment. Additional screening procedures include medical, surgical, and medication history; a buccal swab for germ-line mutation analysis; complete physical examination; vital signs; Eastern Cooperative Oncology Group (ECOG) performance status (PS); 12-lead electrocardiogram (ECG); left ventricular ejection fraction (LVEF); clinical laboratory assessments (hematology, chemistry, coagulation, urinalysis, and serum pregnancy test); bone marrow biopsy and/or aspirate; and blood and bone marrow samples for 2-HG measurement and other exploratory assessments. In addition, subjects in the dose escalation phase will have urine samples for 2 HG measurement and blood samples for determination of plasma cholesterol and 4β-OH-cholesterol levels during screening.

Dose Escalation Phase:

Three days prior to starting the daily dosing of COMPOUND 2 (Day −3), the first 3 subjects enrolled in each cohort in the dose escalation phase will receive a single dose of COMPOUND 2 in clinic and have serial blood and urine samples obtained for determination of concentrations of COMPOUND 2 and 2-HG. A full 72-hour PK/PD profile will be conducted: subjects will be required to remain at the study site for 10 hours on Day −3 and return on Days −2, −1, and 1 for 24, 48, and 72 hour samples, respectively. Daily treatment with COMPOUND 2 will begin on C1D1; subjects in the dose escalation phase who did not undergo the Day −3 PK/PD assessments are to remain in clinic for 4 hours after the C1D1 dose for clinical observation.

Subjects in the dose escalation phase also will undergo PK/PD assessments over a 10-hour period on both C1D15 and C2D1. Additional pre-dose urine and/or blood sampling will be conducted on C1D8, C1D22, C2D15, C3D1, C3D15, and on Day 1 of all subsequent cycles for determination of COMPOUND 2 and 2-HG concentration. Available bone marrow biopsy samples also will be assessed for 2-HG levels.

Expansion Phase:

Subjects in the expansion phase are not required to undergo the Day −3 assessments; these subjects will undergo an 8-hour PK/PD profile conducted on Day 1 of Cycles 1 and 2. Additional blood samples for PK/PD assessments will be drawn pre-dose (within 30 minutes) on Days 8 and 15 of Cycle 1, Day 1 of Cycle 3, on Day 1 of all subsequent cycles, and at the End of Treatment visit. Time-matched 12-lead ECGs will be conducted in triplicate on Day 1 of Cycles 1 and 2; a triplicate ECG also will be conducted at the End of Treatment visit. Single 12-lead ECGs will be conducted at Screening, 4 hours post-dose on Days 8 and 15 of Cycle 1, on Day 1 of every cycle beginning with Cycle 3, and at the Follow-up visit. Available bone marrow biopsy samples will be assessed for 2-HG levels.

Other Safety Assessments:

All subjects will undergo safety assessments during the treatment period to include physical examination, vital signs, ECOG PS, 12-lead ECGs, LVEF, and clinical laboratory assessments (hematology, chemistry, coagulation, urinalysis, and pregnancy testing).

Clinical Activity Assessments:

All subjects will have the extent of their disease assessed, including bone marrow biopsies and/or aspirates and peripheral blood, at screening, on Day 15 (dose escalation phase only), on Day 29, every 28 days thereafter through Month 12, and then every 56 days thereafter while on study drug treatment, independent of dose delays and/or dose interruptions, and/or at any time when progression of disease is suspected. Note that the Day 15 bone marrow evaluation during dose escalation should not be used to determine study treatment continuation status. Response to treatment and treatment decisions in all subjects will be determined by the Investigators based on modified International Working Group (IWG) response criteria or other appropriate response criteria for the malignancy under study. For subjects with relapsed or refractory AML enrolled in the expansion phase, response also will be assessed by an Independent Review Committee.

End of Treatment and Follow-Up:

Subjects may continue treatment with COMPOUND 2 until disease progression, development of other unacceptable toxicity, confirmed pregnancy, undergoing a hematopoietic stem cell transplant (HSCT), death, withdrawal of consent, lost to follow-up, or Sponsor ending the study, whichever occurs first. Subjects who experience disease progression per the applicable response criteria who are, in the opinion of the Investigator, benefiting from treatment may be allowed to continue on study drug with approval of the Medical Monitor.

All subjects are to undergo an end of treatment assessment (within approximately 5 days of the last dose of study drug); in addition, a follow-up safety assessment is to be scheduled 28 days after the last dose.

Subjects who achieve an adequate response to treatment with COMPOUND 2 and meet other criteria required to undergo HSCT may proceed to HSCT after discontinuation of COMPOUND 2 and will be followed on study for disease evaluation (approximately monthly, as standard of care) and any new bone marrow transplant (BMT) conditioning antineoplastic therapies received until disease relapse, death, withdrawal of consent, lost to follow-up, or end of study. If a subject discontinues COMPOUND 2 to undergo HSCT, but is then deemed ineligible for HSCT, the subject may restart COMPOUND 2 with Medical Monitor approval. Subjects who fail HSCT and have recurrent IDH1-mutant positive disease may be eligible to restart treatment with COMPOUND 2 with Medical Monitor approval.

All subjects, including those who relapse following HSCT and elect not to restart treatment, will enter survival follow-up and will be contacted monthly for assessment of survival status and BMT conditioning antineoplastic therapies since discontinuation of study drug until death, withdrawal of consent, lost to follow-up, or end of study.

Concomitant medications do not need to be avoided while subjects are no longer receiving COMPOUND 2 ie, HSCT or survival follow-up periods).

Number of Subjects (Planned):

It is estimated that approximately 236 subjects will be enrolled in the study.

Assuming that identification of the MTD requires the evaluation of 7 dose levels of AG-120 with 3 to 5 subjects per dose level, with the exception that the MTD requires 6 subjects, then 36 subjects will be enrolled during the dose escalation part of the study.

Four cohorts of approximately 25 subjects each in specific hematologic malignancies (total 100 subjects) will initially be enrolled in the expansion phase of the study with the possible additional enrollment of 100 subjects with relapsed or refractory AML in Arm 1 depending on review of safety and clinical activity at the interim analysis.

Additional subjects may be enrolled during dose escalation, for the replacement of subjects who are not evaluable for the assessment of dose escalation, for evaluation of alternative dosing regimens or for further exploring safety, PK, PK/PD, or preliminary clinical activity used to guide the selection of the RP2D.

Diagnosis and Main Criteria for Inclusion:

Inclusion Criteria:

Subjects must meet all of the following criteria to be enrolled in the study:

Subjects must be ≥18 years of age.

Subjects must have an advanced hematologic malignancy including:

Dose Escalation Phase:

Relapsed and/or primary refractory AML as defined by World Health Organization (WHO) criteria; or Untreated AML, ≥60 years of age and are not candidates for standard therapy due to age, performance status, and/or adverse risk factors, according to the treating physician and with approval of the Medical Monitor;

Myelodysplastic syndrome with refractory anemia with excess blasts (subtype RAEB-1 or RAEB-2), or considered high-risk by the Revised International Prognostic Scoring System (IPSS-R) Greenberg et al. *Blood*. 2012; 120(12): 2454-65 that is recurrent or refractory, or the subject is intolerant to established therapy known to provide clinical benefit for their condition (i.e., subjects must not be candidates for regimens known to provide clinical benefit), according to the treating physician and with approval of the Medical Monitor.

(Subjects with other relapsed and/or primary refractory hematologic cancers, for example CMML, who fulfill the inclusion/excluding criteria may be considered on a case-by case basis, with approval of the Medical Monitor.)

Expansion Phase:

Arm 1: Relapsed or refractory AML, defined as:

Subjects who relapse after transplantation;

Subjects in second or later relapse;

Subjects who are refractory to initial induction or reinduction treatment.

Subjects who relapse within 1 year of initial treatment, excluding patients with favorable-risk status according to NCCN Guidelines, version 1.2015.

Arm 2: Untreated AML who are not candidates for standard therapy due to age, cormorbid condition, performance status, and/or adverse risk factors, according to the Investigator and with approval of the Medical Monitor.

Arm 3: Other non-AML IDH1-mutated relapsed and/or refractory advanced hematologic malignancies, where no standard of care treatment option is available. Such as:

Myelodysplastic syndrome that is recurrent or refractory after having failed hypomethylating agent(s) and with the approval of Medical Monitor.

Relapsed and/or primary refractory CMML with the approval of Medical Monitor

Other non-AML IDH1-mutated relapsed and/or refractory advanced hematologic malignancy, that have failed standard of care or no standard of care treatment option is available according to the Investigator and with the approval of the Medical Monitor.

Arm 4: Relapsed AML patients not eligible for Arm 1 that have failed available standard of care or are unable to receive standard of care due to age, comorbid condition, performance status, and/or adverse risk factors, according to the Investigator and with approval of the Medical Monitor.

Subjects must have documented IDH1 R132 gene-mutated disease
- For subjects in the dose escalation phase, IDH1 mutation may be based on local evaluation. (Centralized testing will be performed retrospectively.)
- For subjects in the expansion phase, central testing of IDH1 gene-mutated disease is required during screening to confirm eligibility.

Subjects must be amenable to serial bone marrow sampling, peripheral blood sampling, and urine sampling during the study.

The diagnosis and evaluation of AML or MDS will be made by bone marrow aspiration and/or biopsy. If an aspirate is unobtainable (i.e., a "dry tap"), the diagnosis may be made from the core biopsy.

Subject must be able to understand and willing to sign an informed consent. A legally authorized representative may consent on behalf of a subject who is otherwise unable to provide informed consent, if acceptable to and approved by the site and/or site's Institutional Review Board (IRB).

Subjects must have ECOG PS of 0 to 2.

Platelet count ≥20,000/μL (Transfusions to achieve this level are allowed.) Subjects with a baseline platelet count of <20,000/μL due to underlying malignancy are eligible with Medical Monitor approval.

Subjects must have adequate hepatic function as evidenced by:
- Serum total bilirubin ≤1.5× upper limit of normal (ULN), unless considered due to Gilbert's disease or leukemic involvement;
- Aspartate aminotransferase (AST), alanine aminotransferase (ALT), and alkaline phosphatase (ALP)<3.0×ULN, unless considered due to leukemic involvement.

Subjects must have adequate renal function as evidenced by:
- Serum creatinine ≤2.0×UL OR
- Creatinine clearance >40 mL/min based on the Cockroft-Gault glomerular filtration rate (GFR) estimation: (140−Age)×(weight in kg)×(0.85 if female)/72×serum creatinine Subjects must be recovered from any clinically relevant toxic effects of any prior surgery, radiotherapy, or other therapy intended for the treatment of cancer. (Subjects with residual Grade 1 toxicity, for example Grade 1 peripheral neuropathy or residual alopecia, are allowed with approval of the Medical Monitor.)

Female subjects with reproductive potential must agree to undergo medically supervised pregnancy test prior to starting study drug. The first pregnancy test will be performed at screening (within 7 days prior to first study drug administration), and on the day of the first study drug administration and confirmed negative prior to dosing and Day 1 before dosing all subsequent cycles.

Female subjects with reproductive potential must have a negative serum pregnancy test within 7 days prior to the start of therapy. Subjects with reproductive potential are defined as sexually mature women who have not undergone a hysterectomy, bilateral oophorectomy or tubal occlusion or who have not been naturally postmenopausal (i.e., who have not menstruated at all) for at least 24 consecutive months (i.e., has had menses at any time in the preceding 24 consecutive months). Females of reproductive potential as well as fertile men and their partners who are female of reproductive potential must agree to abstain from sexual intercourse or to use two highly effective forms of contraception from the time of giving informed consent, during the study and for 90 days (females and males) following the last dose of COMPOUND 2. A highly effective form of contraception is defined as hormonal oral contraceptives, injectables, patches, intrauterine devices, double-barrier method (e.g., synthetic condoms, diaphragm, or cervical cap with spermicidal foam, cream, or gel), or male partner sterilization.

Exclusion Criteria:

Subjects who meet any of the following criteria will not be enrolled in the study:

Subjects who previously received prior treatment with a mutant-specific IDH1 inhibitor and progressed on therapy.

Subjects who have undergone hematopoietic stem cell transplant (HSCT) within 60 days of the first dose of COMPOUND 2, or subjects on immunosuppressive therapy post HSCT at the time of screening, or with clinically significant graft-versus-host disease (GVHD). (The use of a stable dose of oral steroids post HSCT and/or topical steroids for ongoing skin GVHD is permitted with Medical Monitor approval.)

Subjects who received systemic anticancer therapy or radiotherapy <14 days prior to their first day of study drug administration. (Hydroxyurea is allowed prior to enrollment and after the start of COMPOUND 2 for the control of peripheral leukemic blasts in subjects with leukocytosis (white blood cell [WBC] counts >30,000/μL).

Subjects who received an investigational agent <14 days prior to their first day of study drug administration. In addition, the first dose of COMPOUND 2 should not occur before a period ≥5 half-lives of the investigational agent has elapsed.

Subjects taking sensitive cytochrome P450 (CYP) 3A4 substrate medications are excluded from the study unless they can be transferred to other medications within ≥5 half-lives prior to dosing, or unless the medications can be properly monitored during the study.

Subjects taking P-glycoprotein (P-gp) transporter-sensitive substrate medications are excluded from the study unless they can be transferred to other medications within ≥5 half-lives prior to dosing, or unless the medications can be properly monitored during the study.

Subjects for whom potentially curative anticancer therapy is available.

Subjects who are pregnant or breast feeding.

Subjects with an active severe infection that required anti-infective therapy or with an unexplained fever >38.5° C. during screening visits or on their first day of study drug administration (at the discretion of the Investigator, subjects with tumor fever may be enrolled).

Subjects with known hypersensitivity to any of the components of COMPOUND 2.

Subjects with New York Heart Association (NYHA) Class III or IV congestive heart failure or LVEF <40% by echocardiogram (ECHO) or multi-gated acquisition (MUGA) scan obtained within approximately 28 days of C1D1.

Subjects with a history of myocardial infarction within the last 6 months of screening.

Subjects with known unstable or uncontrolled angina pectoris.

Subjects with a known history of severe and/or uncontrolled ventricular arrhythmias.

Subjects with QTc interval ≥450 msec or with other factors that increase the risk of QT prolongation or arrhythmic events (e.g., heart failure, hypokalemia, family history of long QT interval syndrome) at screening. Subjects with bundle branch block and a prolonged QTc interval should be reviewed by the Medical Monitor for potential inclusion.

Subjects taking medications that are known to prolong the QT interval unless they can be transferred to other medications within ≥5 half-lives prior to dosing or unless the medications can be properly monitored during the study.

Subjects with known infection with human immunodeficiency virus (HIV) or active hepatitis B or C.

Subjects with any other medical or psychological condition, deemed by the Investigator to be likely to interfere with a subject's ability to sign informed consent, cooperate, or participate in the study.

Subjects with known dysphagia, short-gut syndrome, gastroparesis, or other conditions that limit the ingestion or gastrointestinal absorption of drugs administered orally.

Subjects with clinical symptoms suggesting active central nervous system (CNS) leukemia or known CNS leukemia. Evaluation of cerebrospinal fluid is only required if there is a clinical suspicion of CNS involvement by leukemia during screening.

Subjects with immediately life-threatening, severe complications of leukemia such as uncontrolled bleeding, pneumonia with hypoxia or shock, and/or disseminated intravascular coagulation.

Investigational product, dosage and mode of administration

COMPOUND 2 will be provided as 10, 50, 200, and 250 mg strength tablets to be administered orally.

The first 3 subjects in each dose escalation cohort in the dose escalation portion of the study will receive a single dose of study drug on Day −3; their next dose of study drug will be administered on C1D1 at which time subjects will start dosing daily on Days 1 to 28 in 28-day cycles, with plans to explore alternative dosing regimens if warranted. Starting with C1D1, dosing is continuous; there are no inter-cycle rest periods. Subjects who are not required to undergo the Day −3 PK/PD assessments will initiate daily dosing with COMPOUND 2 on C1D1.

The dose of COMPOUND 2 administered to a subject will be dependent upon which dose cohort is open for enrollment when the subject qualifies for the study. The starting dose of AG-120 to be administered to the first cohort of subjects in the dose escalation phase is 100 mg administered orally twice a day (200 mg/day). The starting dose and regimen for subjects in the expansion phase (500 mg QD) was based on safety, PK, PK/PD, and clinical activity results from the dose-escalation phase of the study will be provided as 10, 50 and 200 mg strength tablets to be administered orally.

Duration of Treatment:

Subjects may continue treatment with COMPOUND 2 until disease progression, development of other unacceptable toxicity, confirmed pregnancy, undergoing HSCT, death, withdrawal of consent, lost to follow-up, or Sponsor ending the study, whichever occurs first. Subjects who experience disease progression per the applicable response criteria who are, in the opinion of the Investigator, benefiting from treatment may be allowed to continue on study drug with approval of the Medical Monitor.

End of Study:

End of study is defined as the time at which all subjects have discontinued treatment with COMPOUND 2 and have been followed for survival for at least 12 months, or have died, been lost to follow up, or withdrew consent prior to 12 months of follow-up.

Criteria for Evaluation:

Safety:

Monitoring of AEs, including determination of DLTs, serious adverse events (SAEs), and AEs leading to discontinuation; safety laboratory parameters; physical examination findings; vital signs; 12-lead ECGs; LVEF; and ECOG PS.

The severity of AEs will be assessed by the NCI CTCAE, version 4.03.

Pharmacokinetics and Pharmacodynamics:

Serial blood sampling for determination of concentration-time profiles of COMPOUND 2. Blood and bone marrow sampling for determination of 2-HG levels. Urine sampling for determination of urinary concentrations of COMPOUND 2 and 2-HG levels (dose escalation subjects only).

Clinical Activity:

Serial blood and bone marrow sampling to determine response to treatment based on modified IWG response criteria in AML or other appropriate response criteria based on the malignancy under study.

Response to treatment as assessed by the site Investigators using modified IWG or other appropriate response criteria for the disease under study will be tabulated. Response will be summarized by best objective response categories, complete remission rate (CRR), and objective response rate (ORR), including all responses of CR, CRp, mCR (morphologic leukemia-free state [MLFS] for subjects with AML), CRi, and PR. Other measures of clinical activity, including duration of complete remission, duration of response, event-free survival, overall survival, and time to remission/response will be summarized.

The primary analysis of the clinical activity of COMPOUND 2 for the expansion phase will be based on Investigator review of response (CRR, ORR, and duration of remission/response) using the Full Analysis Set. Key supportive analyses will be based on the central independent review. Additional efficacy analyses may be conducted using the Efficacy Analysis Set.

Figure 8:
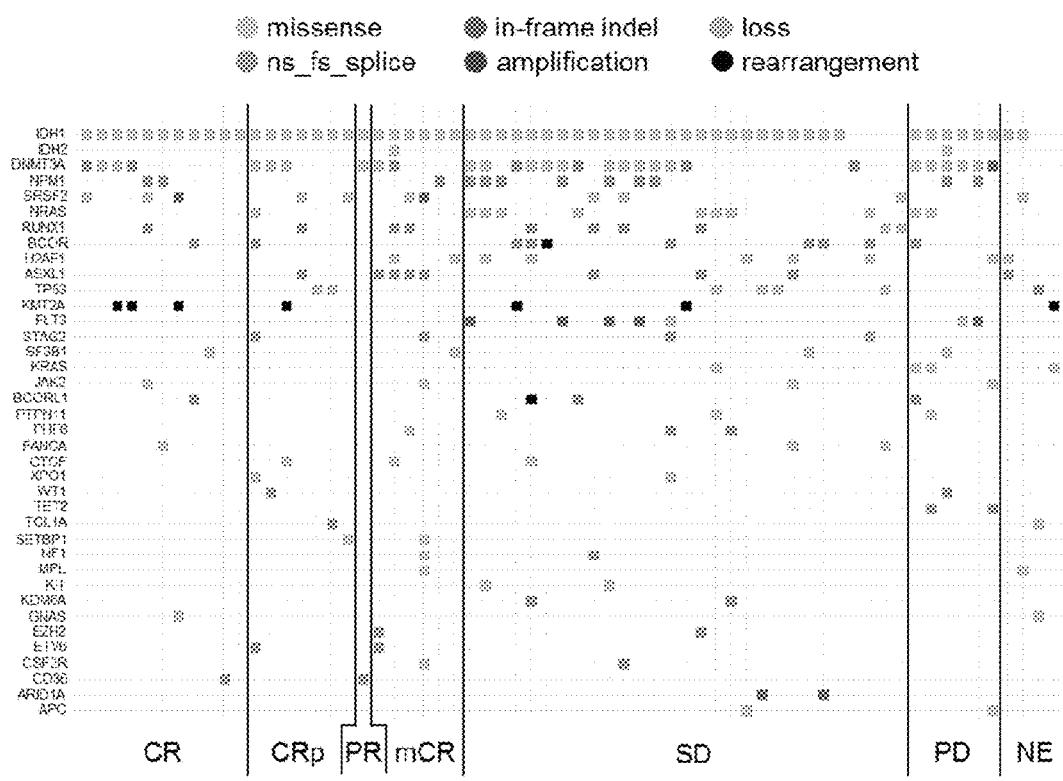
FIG. 8 illustrates the comutations, including NRAS mutations in samples treated with for COMPOUND 2 according to response categories.

A analysis of a subset of the clinical samples from the trial for COMPOUND 2 was conducted. FIG. 8 provides a visual of FLT mutations according to response categories for COMPOUND 2. FIG. 8 profiles bone marrow at screening visit for patients only where genes were mutated in ≥2. In FIG. 8, genes (y-axis) are shown in decreasing order of frequency, with the exception of IDH2, while patients (x-axis) are grouped by response then by similarity in alterations; only patients from dose escalation phase with an evaluable response included.

Response to treatment as assessed by the site Investigators using modified IWG or other appropriate response criteria for the disease under study will be tabulated. Response will be summarized by best objective response categories, complete remission rate (CRR), and objective response rate (ORR), including all responses of CR, CRp, mCR (morphologic leukemia-free state [MLFS] for subjects with AML), CRi, and PR. Other measures of clinical activity, including duration of complete remission, duration of response, event-free survival, overall survival, and time to remission/response will be summarized.

The primary analysis of the clinical activity of COMPOUND 2 for the expansion phase will be based on Investigator review of response (CRR, ORR, and duration of remission/response) using the Full Analysis Set. Key supportive analyses will be based on the central independent review. Additional efficacy analyses may be conducted using the Efficacy Analysis Set.

Example 4: Analysis of a Sample Set

A subset of the clinical samples from the trial for COMPOUND 2 described in Example 3 was analyzed for mutations in the samples. FIG. 8 provides a visual of comutations, including NRAS mutations according to response categories for COMPOUND 2. FIG. 8 profiles bone marrow at screening visit for patients only where genes were mutated in ≥2. In FIG. 8, genes (y-axis) are shown in decreasing order of frequency, with the exception of IDH2, while patients (x-axis) are grouped by response then by similarity in alterations; only patients from dose escalation phase with an evaluable response included.

In certain embodiments, the patients with AML characterized by somatic mutations in NRAS are resistant to treatment of COMPOUND 2.

In certain embodiments, a combination therapy with COMPOUND 2 and one or more compounds that target RAS pathways (e.g. MEK compounds including Trametinib, Selumetinib, Binimetinib, PD-325901, Cobimetinib, CI-1040 or PD035901) is effective in treating AML in patients with AML characterized by somatic mutations in NRAS.

Example 5: NRAS Mutation Status and COMPOUND 1 Response

FoundationOne Heme panel analysis was performed on 100 screening samples from rrAML patients in the trial described in Example 1. Sample types included peripheral blood and bone marrow.

When individual mutations were grouped by gene and analyzed relative to overall response rate (ORR) to COMPOUND 1, a numerically lower ORR was observed in patients with co-occurring mutations in several genes commonly mutated in AML, including SRSF2 (34%), ASXL1 (39%), RUNX1 (26%) and NRAS (19%); however, no statistically significant association between ORR was identified for any mutated gene (Table 10). While rare, co-occurring mutations in TET2 (5 patients) and IDH1 (4 patients) were also observed in this cohort. Mechanistically, mutations in these genes may counteract the efficacy of COMPOUND 1; however, presence of either of these mutated genes was not associated with significant decrease in ORR or complete response (CR) (Table 10).

TABLE 10

Association of known somatic mutations identified by FoundationOne Heme Panel with response to COMPOUND 1

| Gene | R140 (n) | R172 (n) | ORR | ORR, OR | ORR, p-value | CR | CR, OR | CR, p-value |
|---|---|---|---|---|---|---|---|---|
| NRAS | 12 | 5 | 0.188 | 0.270 | 0.0606 | 0.063 | 0.099 | 0.0061 |
| PTPN11 | 5 | 1 | 0.000 | 0.112 | 0.0695 | 0.000 | 0.148 | 0.1590 |
| RUNX1 | 21 | 3 | 0.261 | 0.411 | 0.1115 | 0.217 | 0.429 | 0.1616 |
| SRSF2 | 45 | 0 | 0.341 | 0.598 | 0.2056 | 0.293 | 0.637 | 0.2694 |
| ASXL1 | 21 | 6 | 0.385 | 0.784 | 0.6693 | 0.269 | 0.583 | 0.2785 |
| SETBP1 | 3 | 0 | 0.000 | 0.180 | 0.2584 | 0.000 | 0.237 | 0.2973 |
| SF3B1 | 2 | 1 | 0.000 | 0.180 | 0.2584 | 0.000 | 0.237 | 0.2973 |
| JAK2 | 3 | 1 | 0.000 | 0.138 | 0.1334 | 0.000 | 0.182 | 0.2978 |
| FLT3 | 11 | 1 | 0.200 | 0.306 | 0.1892 | 0.200 | 0.408 | 0.3267 |
| CEBPA | 6 | 0 | 0.167 | 0.250 | 0.2347 | 0.167 | 0.331 | 0.4150 |
| BCORL1 | 2 | 0 | 0.000 | 0.254 | 0.5056 | 0.000 | 0.334 | 0.5315 |
| ETV6 | 1 | 1 | 0.500 | 1.306 | 1.0000 | 0.000 | 0.334 | 0.5315 |
| GATA2 | 2 | 0 | 0.000 | 0.254 | 0.5056 | 0.000 | 0.334 | 0.5315 |
| TP53 | 3 | 0 | 0.000 | 0.254 | 0.5056 | 0.000 | 0.334 | 0.5315 |
| STAG2 | 10 | 2 | 0.455 | 1.091 | 1.0000 | 0.455 | 1.462 | 0.5366 |
| NPM1 | 15 | 0 | 0.417 | 0.924 | 1.0000 | 0.250 | 0.548 | 0.5383 |
| KMT2A | 12 | 2 | 0.357 | 0.703 | 0.5874 | 0.286 | 0.662 | 0.5757 |
| EZH2 | 5 | 0 | 0.200 | 0.316 | 0.3892 | 0.200 | 0.418 | 0.6526 |
| KRAS | 3 | 2 | 0.400 | 0.864 | 1.0000 | 0.200 | 0.418 | 0.6526 |
| BCOR | 10 | 5 | 0.385 | 0.800 | 0.7779 | 0.308 | 0.743 | 0.7696 |
| ATM | 3 | 0 | 0.500 | 1.306 | 1.0000 | 0.500 | 1.721 | 1.0000 |
| CBL | 3 | 0 | 0.333 | 0.646 | 1.0000 | 0.333 | 0.853 | 1.0000 |
| CUX1 | 2 | 0 | 0.500 | 1.306 | 1.0000 | 0.500 | 1.721 | 1.0000 |
| DNMT3A | 28 | 14 | 0.513 | 1.509 | 0.2745 | 0.359 | 0.945 | 1.0000 |
| IDH1 | 4 | 0 | 0.500 | 1.310 | 1.0000 | 0.250 | 0.563 | 1.0000 |
| PHF6 | 6 | 0 | 0.500 | 1.314 | 1.0000 | 0.333 | 0.850 | 1.0000 |
| TET2 | 5 | 0 | 0.333 | 0.646 | 1.0000 | 0.333 | 0.853 | 1.0000 |
| U2AF1 | 1 | 1 | 1.000 | 6.678 | 0.1873 | 0.500 | 1.721 | 1.0000 |
| WT1 | 2 | 1 | 0.333 | 0.646 | 1.0000 | 0.333 | 0.853 | 1.0000 |

Figure 9A:
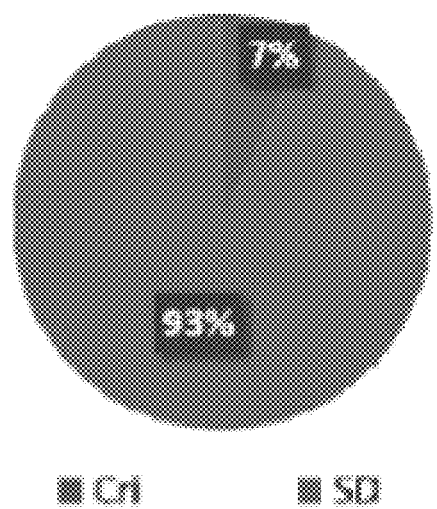
FIG. 9A provides a pie chart indicating proportion of responses seen in 14 patients with NRAS co-mutations.

In contrast to ORR, significantly fewer patients with co-occurring NRAS mutations achieved CR following treatment with COMPOUND 1 (p=0.0061, Table 10). To further investigate the association between NRAS mutations and ORR to COMPOUND 1, a more detailed analysis of individual mutation sites was performed. NRAS mutations at G12, G13, and Q61 are the most highly characterized sites known to result in constitutive RAS signaling, see Prior I A, Lewis P D, Mattos C. A comprehensive survey of Ras mutations in cancer, *Cancer Res.* 2012; 72(10):2457-67. When mutations at these sites were analyzed versus ORR to COMPOUND 1, the observed decrease in ORR became statistically significant (p=0.002, see, FIG. 9A and Table 11). Table 11 provides a contingency table indicating statistical significance of lower overall response rate seen in patients presenting with an NRAS co-mutation.

TABLE 11 mNRAS Contingency Test

| Fisher's Exact test | No Response | Response |
|---|---|---|
| NRAS wt | 37 | 40 |
| NRAS mt | 13 | 1 |

Figure 9:
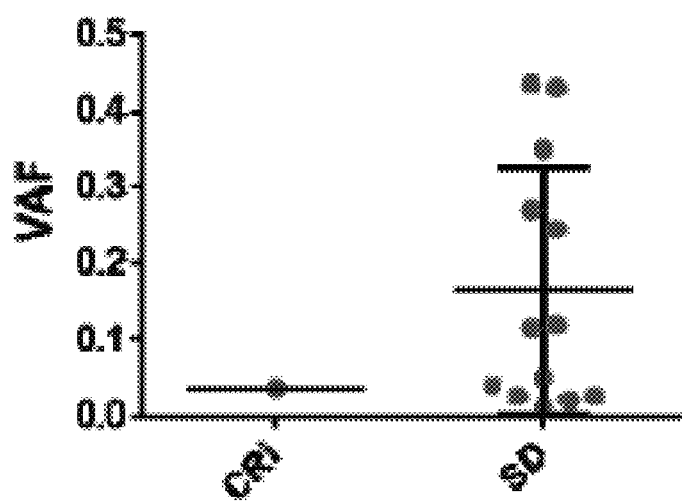
FIGS. 9 A-B illustrate association of NRAS mutations with response to COMPOUND 2.

However, analysis of NRAS variant allele frequency (NRAS VAF) did not indicate an association between VAF and ORR to COMPOUND 1; 19 out of 25 non-responding and 1 out of 1 responding patients with NRAS mutations at G12, G13 or Q61 had a VAF lower than 10% (FIG. 9 B).

Notably, the initial overall analysis of KRAS mutations from the panel did not associate with lower ORR or CR following treatment with COMPOUND 1 (p=1.000 and 0.6526, respectively, Table 10). Further, an analysis of mutations in analogous KRAS amino acids that result in constitutive signaling (G12 or Q61) did not associate with lower CR following treatment with COMPOUND 1 and similar to NRAS, an analysis of the KRAS VAF did not associate with lower ORR or CR (range 0.02 to 0.47).

Figure 10A:
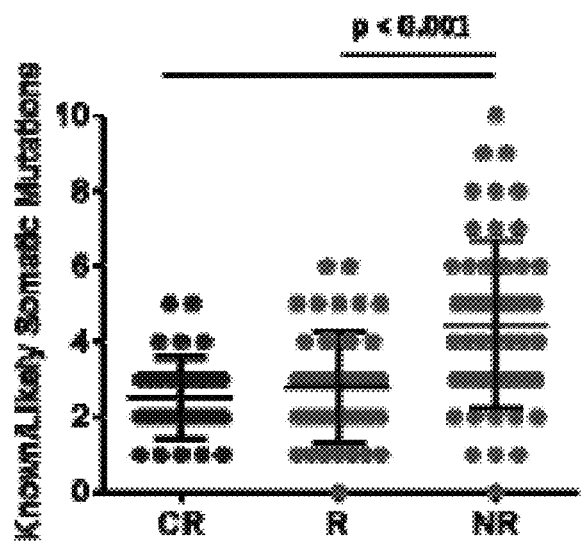
FIG. 10A illustrates number of mutations found per patient separated by response (≥PR). Hash marks represent mean and standard deviation. P-value from student's t-test.
Figure 10B:
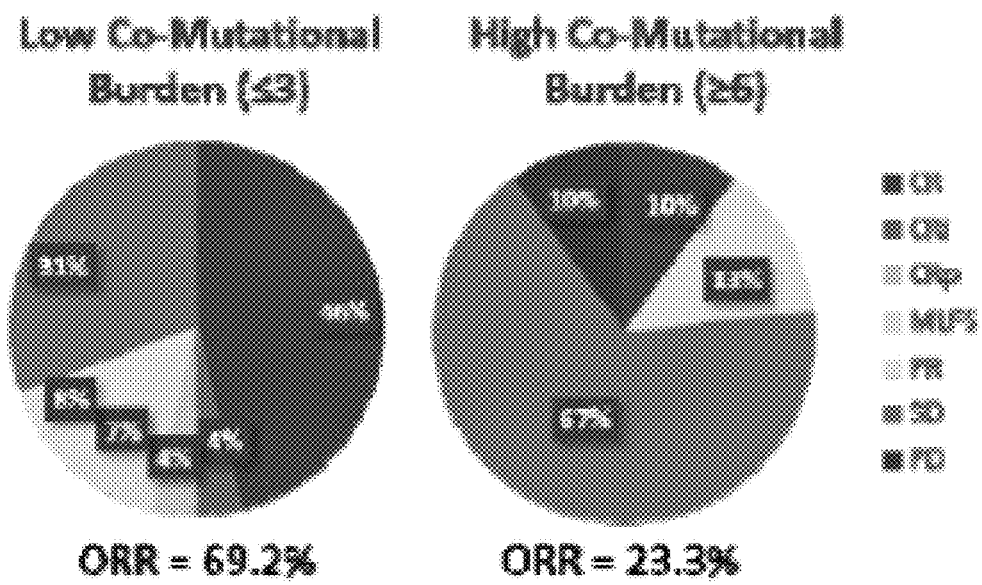
FIG. 10B provides pie charts of response assessment and ORR in patients with the lowest third of mutations (≤3) and highest third (≥6).
Figure 10C:
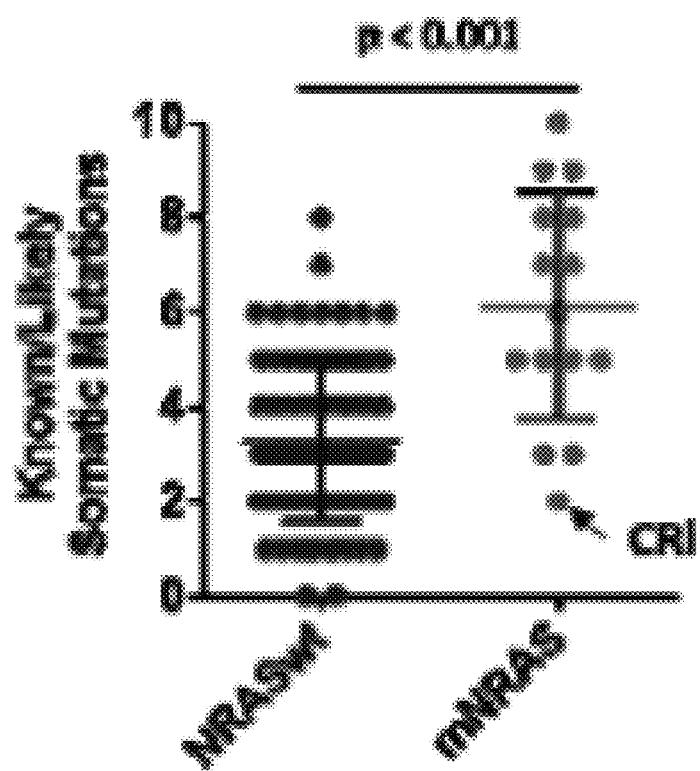
FIG. 10C illustrates number of mutations found per patient separated by presence of G12, G13 or Q61 mNRAS.

Analysis of number of known and likely co-occurring somatic mutations by the FoundationOne Heme panel with response (≥PR) to COMPOUND 1 showed that responders had significantly fewer co-occurring mutations than non-responders (p<0.001, FIG. 10 A). Segregating patients in three equal tertiles based on number of co-occurring mutations (≤3, 3 to 6, and ≥6 co-mutations) revealed a large difference in ORR for patients with the most (≥6) co-occurring mutations compared to patients with the least (≤3) co-occurring mutations (ORR 23.3% vs 69.2%, respectively) (FIG. 10 B). Notably, mutational burden was significantly higher (p<0.001) in patients with NRAS mutations (G12, G13, or Q61), suggesting that the observed decrease in ORR was tracking with overall increased mutational burden in the >400 genes known to be somatically altered in cancer assayed by the FoundationOne Heme Panel (FIG. 10 C).

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method of treating acute myeloid leukemia in a subject comprising administering to the subject a mutant isocitrate dehydrogenase 2 (IDH2) inhibitor 2-methyl-1-[(4-[6-(trifluoromethyl)pyridin-2-yl]-6-[2-(trifluoromethyl)pyridin-4-yl]amino-1,3,5-triazin-2-yl)amino]propan-2-ol having the following formula:

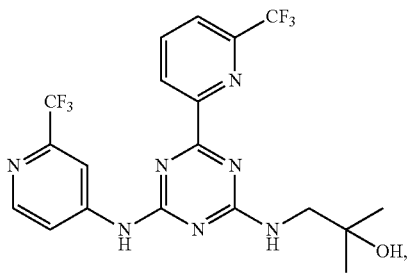 [SMILES: CC(C)(O)CNc1nc(Nc2ccnc(C(F)(F)F)c2)nc(-c2cccc(C(F)(F)F)n2)n1]

or a pharmaceutically acceptable salt, solvate, or tautomer thereof, wherein the acute myeloid leukemia is characterized by the presence of a mutant allele of IDH2 and the absence of a mutant allele of NRAS.

2. The method of claim 1, wherein the mutant allele of IDH2 is IDH2 R140Q or R172K.

3. The method of claim 1, wherein the acute myelogenous leukemia is relapsed or refractory acute myelogenous leukemia, characterized by the presence of a mutant allele of IDH2.

4. The method of claim 1, wherein 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate or tautomer thereof is administered in a dose of about 20 to 2000 mg/day.

5. The method of claim 4, wherein 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol or a pharmaceutically acceptable salt, solvate or tautomer thereof is administered in a dose of about 50 to 500 mg/day.

6. The method of claim 1, wherein the subject has 3 or less co-occuring mutations.

7. The method of claim 1, wherein the mutant isocitrate dehydrogenase 2 (IDH2) inhibitor is 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

8. The method of claim 1, wherein the mutant isocitrate dehydrogenase 2 (IDH2) inhibitor is a mesylate salt of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol.

* * * * *